US010369171B2

(12) United States Patent
Kim et al.

(10) Patent No.: US 10,369,171 B2
(45) Date of Patent: Aug. 6, 2019

(54) ATTENUATED REOVIRUSES FOR SELECTION OF CELL POPULATIONS

(75) Inventors: Manbok Kim, Gainesville, FL (US); Derrick E. Rancourt, Calgary (CA); Nicole Zur Nieden, Riverside, CA (US); Randal N. Johnston, Calgary (CA)

(73) Assignee: VIROCURE, INC., Seoul (KR)

( * ) Notice: Subject to any disclaimer, the term of this patent is extended or adjusted under 35 U.S.C. 154(b) by 1053 days.

(21) Appl. No.: 12/075,751

(22) Filed: Mar. 12, 2008

(65) Prior Publication Data
US 2009/0104162 A1 Apr. 23, 2009

Related U.S. Application Data

(60) Provisional application No. 60/906,710, filed on Mar. 13, 2007.

(51) Int. Cl.
*A61K 39/12* (2006.01)
*A61K 35/28* (2015.01)
*A61K 35/765* (2015.01)
*A61K 35/545* (2015.01)

(52) U.S. Cl.
CPC ............ *A61K 35/28* (2013.01); *A61K 35/545* (2013.01); *A61K 35/765* (2013.01); *C12N 2720/12032* (2013.01)

(58) Field of Classification Search
None
See application file for complete search history.

(56) References Cited

U.S. PATENT DOCUMENTS

| | | | |
|---|---|---|---|
| 5,210,272 A | 5/1993 | Palmer | 560/13 |
| 5,344,939 A | 9/1994 | Palmer | 548/531 |
| 6,110,461 A | 8/2000 | Lee et al. | |
| 6,136,307 A | 10/2000 | Lee et al. | |
| 6,261,555 B1 | 7/2001 | Lee et al. | |
| 6,344,195 B1 | 2/2002 | Lee et al. | |
| 6,455,038 B1 | 9/2002 | Lee et al. | |

(Continued)

FOREIGN PATENT DOCUMENTS

| | | |
|---|---|---|
| CA | 2411397 | 5/2004 |
| CA | 2422245 | 9/2004 |

(Continued)

OTHER PUBLICATIONS

Spriggs et al (Nature 297:68-70, 1982).*

(Continued)

*Primary Examiner* — Janet L Andres
*Assistant Examiner* — Stuart W Snyder
(74) *Attorney, Agent, or Firm* — Vorys, Sater, Seymour & Pease LLP; Mih Suhn Koh

(57) ABSTRACT

The present invention relates to methods for killing neoplastic cells, such as ras-activated cancerous cells, in vitro. In particular embodiments, an attenuated reovirus (e.g., a reovirus lacking a wild-type S1 gene) may be administered to a mixed cellular composition comprising cancerous cells and stem cells such as adult stem cells and/or hematopoietic stem cells; in these embodiments, the attenuated reovirus may result in killing of the cancerous cells with little or no damage to the healthy stem cells.

21 Claims, 7 Drawing Sheets
(7 of 7 Drawing Sheet(s) Filed in Color)
Specification includes a Sequence Listing.

(56) References Cited

U.S. PATENT DOCUMENTS

| | | | |
|---|---|---|---|
| 6,528,305 B2 | 3/2003 | Thompson et al. | |
| 6,565,831 B1 | 5/2003 | Coffey et al. | |
| 6,576,234 B2 | 6/2003 | Lee et al. | |
| 6,596,268 B1 | 7/2003 | Coffey et al. | |
| 6,605,589 B1 | 8/2003 | Uckun et al. | 514/2 |
| 6,649,157 B2 | 11/2003 | Coffey et al. | |
| 6,703,232 B2 | 3/2004 | Thompson et al. | |
| 6,808,916 B2 | 10/2004 | Coffey et al. | |
| 6,811,775 B2 | 11/2004 | Lee et al. | |
| 6,994,858 B2* | 2/2006 | Morris et al. | 424/215.1 |
| 7,014,847 B2 | 3/2006 | Coffey et al. | |
| 7,049,127 B2 | 5/2006 | Thompson et al. | |
| 7,122,182 B2 | 10/2006 | Groene et al. | |
| 7,163,678 B2 | 1/2007 | Norman et al. | |
| 7,186,542 B2 | 3/2007 | Coffey et al. | |
| 7,192,580 B2 | 3/2007 | Atkins et al. | 424/93.2 |
| 7,264,798 B2 | 9/2007 | Coffey et al. | |
| 7,270,812 B2 | 9/2007 | Shino et al. | |
| 7,300,650 B2 | 11/2007 | Lee et al. | |
| 7,431,932 B2 | 10/2008 | Morris et al. | 424/215 |
| 7,708,987 B2* | 5/2010 | Coffey et al. | 424/93.2 |
| 2001/0048919 A1 | 12/2001 | Morris et al. | 424/93.21 |
| 2002/0037543 A1 | 3/2002 | Atkins et al. | 435/7.23 |
| 2002/0168344 A1 | 11/2002 | Coffey et al. | |
| 2003/0044384 A1 | 3/2003 | Roberts et al. | |
| 2003/0165465 A1* | 9/2003 | Roberts et al. | 424/93.2 |
| 2004/0005329 A1 | 1/2004 | Uckun et al. | 424/185.1 |
| 2004/0115170 A1 | 6/2004 | Brown et al. | |
| 2004/0126869 A1 | 7/2004 | Thompson | |
| 2004/0146491 A1 | 7/2004 | Norman et al. | |
| 2004/0202663 A1 | 10/2004 | Hu et al. | |
| 2004/0265271 A1 | 12/2004 | Lee et al. | |
| 2005/0019308 A1 | 1/2005 | Normal et al. | |
| 2005/0026289 A1 | 2/2005 | Morris et al. | 435/456 |
| 2005/0063954 A1 | 3/2005 | Lee et al. | |
| 2005/0123513 A1 | 6/2005 | Lee et al. | |
| 2005/0214266 A1 | 9/2005 | Morris et al. | |
| 2006/0029598 A1 | 2/2006 | Morris et al. | |
| 2006/0073166 A1 | 4/2006 | Coffey et al. | |
| 2006/0088869 A1 | 4/2006 | Coffey et al. | |
| 2009/0104162 A1* | 4/2009 | Kim et al. | 424/93.7 |
| 2009/0214479 A1* | 8/2009 | Kim et al. | 424/93.6 |
| 2017/0049824 A1 | 2/2017 | Nordrum et al. | |

FOREIGN PATENT DOCUMENTS

| | | |
|---|---|---|
| CA | 2434995 | 1/2005 |
| CA | 2435967 | 1/2005 |
| CA | 2436196 | 1/2005 |
| CA | 2374388 | 7/2005 |
| WO | WO 1999/008692 | 2/1999 |
| WO | WO 1999/018799 | 4/1999 |
| WO | WO 2000/050051 | 8/2000 |
| WO | WO 2000/062735 | 10/2000 |
| WO | WO 2001/019380 | 3/2001 |
| WO | WO 2001/035970 | 5/2001 |
| WO | WO 2001/083710 | 11/2001 |
| WO | WO 2001/083711 | 11/2001 |
| WO | WO 2002/000233 | 1/2002 |
| WO | WO 2002/011742 | 2/2002 |
| WO | WO 2002//012435 | 2/2002 |
| WO | WO 2002/039117 | 5/2002 |
| WO | WO 2002/040042 | 5/2002 |
| WO | WO 2002/030304 | 6/2002 |
| WO | WO 2002/043647 | 6/2002 |
| WO | WO 2002/066040 | 8/2002 |
| WO | WO 2002/074940 | 9/2002 |
| WO | WO 2002/091997 | 11/2002 |
| WO | WO 2003/080083 | 10/2003 |
| WO | WO 2003/093463 | 11/2003 |
| WO | WO 2003/094938 | 11/2003 |
| WO | WO 2003/094939 | 11/2003 |
| WO | WO 2004/003562 | 1/2004 |
| WO | WO 2004/066947 | 8/2004 |
| WO | WO 2005/002607 | 1/2005 |
| WO | WO 2005/014017 | 2/2005 |
| WO | WO 2007/099401 | * 9/2007 |
| WO | WO 2008/112911 | 9/2008 |

OTHER PUBLICATIONS

Imani et al (PNAS 85:7887-7891, 1988).*

Thirukkumaran et al. (Reovirus oncolysis as a novel purging strategy for autologous stem cell transplantation. Blood, 2003; 102(1): 377-387 (Year: 2003).*

Kim et al. (Acquired resistance to reoviral oncolysis in Ras-transformed fibrosarcoma cells. Oncogene, 2007; 26: 4124-4134 (Year: 2007).*

Amit et al. (Clonally Derived Human Embryonic Stem Cell Lines Maintain Pluripotency and Proliferative Potential for Prolonged Periods of Culture. Develop. Biol. 2000; 227: 271-278 (Year: 2000).*

ME Wilcox (Evaluation of Reovirus as an Oncolytic Agent in Malignant Gliomas. A Dissertation Submitted to the Faculty of Graduate Studies in Partial Fulfillment of the Requirements Leadng to a Master of Science Degree, Department of Medical Science, Calgary, Alberta, May 2000 (Year: 2000).*

Thirukkumaran et al. Reovirus oncolysis as a novel purging strategy for autologous stem cell transplantation. Blood, 2003; 102(1): 377-387.*

Wu et al. Biological Purging of Breast Cancer Cells Using an Attenuated Replication-competent Herpes Simplex Virus in Human Hematopoietic Stem Cell Transplantation. Cancer Res. 2001; 61: 3009-3015.*

Kim et al. Acquired resistance to reoviral oncolysis in Ras-transformed fibrosarcoma cells. Oncogene, 2007; 26: 4124-4134.*

Amit et al. Clonally Derived Human Embryonic Stem Cell Lines Maintain Pluripotency and Proliferative Potential for Prolonged Periods of Culture. Develop. Biol. 2000; 227: 271-278.*

ME Wilcox, Evaluation of Reovirus as an Oncolytic Agent in Malignant Gliomas. A Dissertation Submitted to the Faculty of Graduate Studies in Partial Fulfillment of the Requirements Leadng to a Master of Science Degree, Department of Medical Science, Calgary, Alberta, May 2000.*

Alain et al., "Reovirus decreases azoxymethane-induced aberrant crypt foci and colon cancer in a rodent model," *Cancer Gene Ther.*, 14:867-72, 2007.

Alain et al., "Reovirus therapy of lymphoid malignancies" *Blood*, 100:4146-53, 2002.

Alain et al., "The oncolytic effect in vivo of reovirus on tumour cells that have survived reovirus cell killing in vitro," *British Journal of Cancer*, 95:1020-1027, 2006.

Chandran et al., "Complete in vitro assembly of the reovirus outer capsid produces highly infectious particles suitable for genetic studies of the receptor-binding protein," *J. Virol.*, 75:5335-5342, 2001.

Chandran et al., "Strategy for nonenveloped virus entry: a hydrophobic conformer of the reovirus membrane penetration protein micro 1 mediates membrane disruption," *J. Virol.*, 76:9920-9933, 2002.

DeBiasi et al., "Caspase inhibition protects against reovirus-induced myocardial injury in vitro and in vivo," *J. Virol.*, 78:11040-11050, 2004.

Hoyt et al., "Nonstructural protein sigma1s is a determinant of reovirus virulence and influences the kinetics and severity of apoptosis induction in the heart and central nervous system," *J. Virol.*, 79:2743-2753, 2005.

Kim et al., "Acquired resistance to reoviral oncolysis in Ras-transformed fibrosarcoma cells," *Oncogene*, 26:4124-34, 2007.

Kim et al., "Caspar, a suppressor of antibacterial immunity in Drosophila," *Proc. Natl. Acad. Sci. USA*, 103:16358-16363, 2006.

Kim et al., "Reovirus and tumor oncolysis," *J. Microbiol.*, 45:187-192, 2007.

Loken et al., "Morbidity in immunosuppressed (SCID/NOD) mice treated with reovirus (dearing 3) as an anti-cancer biotherapeutic," *Cancer Biol. Ther.*, 3:734-738, 2004.

(56) References Cited

OTHER PUBLICATIONS

Norman et al., "Reovirus oncolysis: the Ras/RalGEF/p38 pathway dictates host cell permissiveness to reovirus infection," *Proc. Natl. Acad. Sci. USA*, 101:11099-11104, 2004.
PCT International Search Report and Written Opinion, issued in International Application No. PCT/US2008/056881, dated Aug. 25, 2008.
Ring, "Cytolytic viruses as potential anti-cancer agents," *Journal of General Virology*, 83:491-502, 2002.
Takahashi et al., "Role of ERas in promoting tumour-like properties in mouse embryonic stem cells," *Nature*, 423:541-555, 2003.
Terheggen et al., "Myocarditis associated with reovirus infection," *Eur. J. Clin. Microbiol. Infect. Dis.*, 22:197-198, 2003.
Thirukkumaran et al., "Biological purging of breast cancer cell lines using a replication-competent oncolytic virus in human stem cell autografts," *Bone Marrow Transplant.*, 35:1055-64, 2005.
Wilcox et al., "Reovirus as an oncolytic agent against experimental human malignant gliomas," *J. Natl. Cancer Inst.*, 93:903-12, 2001.
Yang et al., "Efficacy and safety evaluation of human reovirus type 3 in immunocompetent animals: racine and nonhuman primates," *Clin. Cancer Res.*, 10:8561-76, 2004.
Yang et al., "Reovirus as an experimental therapeutic for brain and leptomeningeal metastases from breast cancer," *Gene Therapy*, 11:1579-1589, 2004.
Ahmed et al., "Role of the S4 gene in the establishment of persistent reovirus infection in L cells", *Cell*, 28 (3): 605-612, 1982.
Baer et al., "Mutations in reovirus outer-capsid protein sigma3 selected during persistent infections of L cells confer resistance to protease inhibitor E64,"*J. Virol.*, 71 (7): 4921-4928, 1997.
Baer et al., "Mutant cells selected during persistent reovirus infection do not express mature cathespin L and do not support reovirus disassembly,"Journal of Virology, 73 (11): 9532-9543, 1999.
Brown et al., "Bioengineering the oncolytic potential of reovirus," *Gene Therapy*, 8 (1):s7, 2001.
Campbell et al., "Junctional Adhesion Molecule A Serves as a Receptor for Prototype and Field-Isolate Strains of Mammalian Reovirus," *J. of Virol.*, 19 (13): 7967-7978, 2005.
Chandran et al., "In vitro recoating of reovirus cores with baculovirus-expressed outer-capsid proteins mu1 and sigma3," *J. Virol.*, 73: 3941, 1999.
Chapell et al., "Identification of carbohydrate-binding domains in the attachment proteins of type 1 and type 3 reoviruses,"*J. Virol.*, 74 (18): 8472-8479, 2000.
Chapell et al., "Mutations in type 3 reovirus that determine binding to sialic acid are contained in the fibrous tail domain of viral attachment protein sigma 1,"*J. Virol.*, 71 (3): 1834-1841, 1997.
Chiocca, "Oncolytic viruses," *Nature Reviews Cancer*, 2 (12): 938-950, 2002.
Clarke et al., "Mechanisms of reovirus-induced cell death and tissue host-cell signaling and trariscription factor activation" *Viral Immunology*, 18 (1):89-115, 2004.
Clarke et al., "Reovirus infection activates JNK and the JNK-dependent transcription factor c-jun," *Journal of Virology*, 75 (23): 1275-11283, 2001.
Coffey et al., "Reovirus therapy of tumors with activated Ras pathway," *Science*, 282 (5392): 1332-1334, 1998.
Connolly et al., "Reovirus binding to cell surface sialic acid potentiates virus-induced apoptosis," *J. Virol.*, 75 (9): 4029-4039, 2001.
Dermody et al., "Eradication of persistent reovirus infection from a B-cell hybridoma,"*Virol.*, 212 (1): 272-276, 1995.
Dermody et al., "Sequence Diversity in S1 Genes and S1 Translation Products of 11 Serotype 3 Reovirus Strains," *J. Virol.*, 64 (10): 4842-4850, 1990.
Dermody et al., "Cells and viruses with mutations affecting viral entry are selected during persistent infections of L cells with mammalian reoviruses," *J. Virol.*, 67 (4): 2055-2063, 1993.
Dermody, "Molecular Mechanisms of Persistent Infection by Reovirus," *Current Topics in Microbiology and Immunology*, 233 (2): 1-22, 1998.

Ducan et al., "Conformational and functional analysis of the C-terminal globular head of the reovirus cell attachment protein," *Virology*, 182 (2): 810-819, 1991.
Ebert et al., "Cathespin B is inhibited in mutant cells selected during persistent reovirus infection," *The Journal of Biological Chemist*, 279 (5): 3837-3851, 2004.
Everts at al., "Replication-selective oncolytic viruses in the treatment of cancer," *Cancer Gene Therapy*, 12 (2): 141-161, 2005.
Genebank Accession No. K02739.
Genebank Accession No. L37677.
Genebank Accession No. M35963.
Genebank Accession No. M35964.
Genebank Accession No. X01161.
Haller et al., "Genetic mapping of reovirus virulence and organ tropism in severe combined immunodeficient mice: organ-specific virulence genes," *J. Virol.*, 29 (1): 357-364, 1995.
Helander et al., "Protective Immunoglobulin A and G Antibodies Bind to Overlapping Intersubunit Epitopes in the Head Domain of Type 1 Reovirus Adhesin σ1," *J. Virol.*, 78 (19): 10695-10705, 2004.
International Preliminary Report on Patentability, issued in International Application No. PCT/IB2006/004149, dated Feb. 5, 2008.
International Search Report and Written Opinion, issued in international Application No. PCT/IB2006/004149, dated Dec. 13, 2007.
Kaye et al., Genetic basis for altered pathogenesis of an immune-selected antigenic variant of reovirus type 3 (Dearing), *J. Virol.*, 59 (1): 90-97, 1986
Larson et al., "Reovirus exists in the form of 13 particle species that differ in their content of protein sigma 1," *Virology*, 201 (2):303-311, 1994.
Lee et al., "Protein sigma 1 is the reovirus cell attachment protein," *Virology*, 108 (1): 156-163, 1981.
Lee et al., "Reovirus protein sigma 1: from cell attachment to protein oligomerization and folding mechanisms," *Bioessays*, 16 (3): 199-206, 1994.
Leone et al., "The N-terminal heptad repeat region of reovirus cell attachment protein sigma 1 is responsible for sigma 1 oligomer stability and possesses intrinsic oligomerization function," *Virology*, 182 (1): 336-345, 1991.
Leone et al., "The reovirus cell attachment protein possesses two independently active trimerization domains: basis of dominant negative effects," *Cell*, 71 (3): 479-488, 1992.
Mah et al., "The N-terminal quarter or reovirus cell attachment protein sigma 1 possesses intrinsic virion-anchoring function," *Virology*, 179 (1): 95-103, 1990.
Monks et al., "Feasibility of a high-flux anticancer drug screen using a diverse panel of cultured human tumor cell lines," *J. Nat. Canc. Inst.*, 83 (11) 757-766, 1991.
Mullen et al., "Viral oncolysis," *Oncologist*, 7 (2): 106-119, 2002.
Nagata et al., "Analysis of functional domains on reovirus cell attachment protein sigma 1 using cloned S1 gene deletion mutants," *Virology*, 160 (1): 162, 1987.
Russell, "RNA viruses as virotherapy agents," *Cancer Gene Therapy*, 9 (12): 961-966, 2002.
Strong et al., "The molecular basis of viral oncolysis: usurpation of the Ras signaling pathway by reovirus," *EMBO J.* 17 (12): 3351-3362, 1998.
Turner et al., "Site-directed mutagenesis of the C-terminal portion of reovirus protein sigma-1: evidence for a conformation-dependent receptor bidning domain," Virology, 186 (1): 219-227, 1992.
Tyler et al., "Reoviruses and the host cell,"*Trends in Microbiology*, 9 (11): 560-564, 2001.
Weiner et al., "Absolute linkage of virulence and central nervous system cell tropism of reoviruses to viral hemagglutinin," *J. Infect Dis.*, 141 (5): 609-616, 1980.
Wetzel et al., "Reovirus Variants Selected During Persistent Infections of L Cells Contain Mutations in the Viral S1 and S4 Genes and Are Altered in Viral Disassembly," *J. Virol.*, 71 (2): 1362-1369, 97.
Wickramasinghe et al., "Cathespin B promotes both motility and invasivenesss of oral carcinoma cells," *Arch. Biochem. Biophys.*, 436 (1): 187-195, 2005.

(56) References Cited

OTHER PUBLICATIONS

Wildner et al., "Comparison of replication-selective, oncolytic viruses for the treatment of human cancers," *Current Opinion in Molecular Therapeutics*, 5 (4): 351-361, 2003.

Wilson et al., "Association of the reovirus S1 gene with serotype 3-induced biliary atresia in mice," *J. Virol.*, 68 (10: 6458-6465, 1994.

European Supplemental Search Report, issued in European Application No. 06849494.7-2406, dated Nov. 13, 2009.

Wilson et al., "Persistent reovirus Infections of L cells select sigma-1 that alter oligomer stability," *J. Virol.*, 70: 6598-6606, 1996.

Hoyt, C.C. et al., "Nonstructural Protein σ1 Is a Determinant of Reovirus Virulence and Influences the Kinetics and Severity of Apoptosis Induction in the Hearth and Central Nervous Stem", Journal of Virology 79: 2743-2753, American Society for Microbiology, Washington, DC (Mar. 2005).

Harrington et al., "Clinical Trials with Oncolytic Reovirus: Moving Beyond Phase I into Combinations with Standard Therapeutics," *Cytokine Growth Factor Rev.*, 21(0):91-98, Elsevier Ltd.(2010).

Office Action dated Aug. 23, 2017, in co-pending U.S. Appl. No. 15/246,109, filed Aug. 24, 2006.

Office Action dated Jul. 21, 2017, in co-pending U.S. Appl. No. 11/997,537, §371 (c) date of Oct. 14, 2008.

\* cited by examiner

SEQUENCE LISTING

```
<160> NUMBER OF SEQ ID NOS: 3

<210> SEQ ID NO 1
<211> LENGTH: 455
<212> TYPE: PRT
<213> ORGANISM: Mammalian orthoreovirus 2

<400> SEQUENCE: 1

Met Asp Pro Arg Leu Arg Glu Glu Val Val Arg Leu Ile Ile Ala Leu
1               5                   10                  15

Thr Ser Asp Asn Gly Ala Ser Leu Ser Lys Gly Leu Glu Ser Arg Val
                20                  25                  30

Ser Ala Leu Glu Lys Thr Ser Gln Ile His Ser Asp Thr Ile Leu Arg
            35                  40                  45

Ile Thr Gln Gly Leu Asp Asp Ala Asn Lys Arg Ile Ile Ala Leu Glu
        50                  55                  60

Gln Ser Arg Asp Asp Leu Val Ala Ser Val Ser Asp Ala Gln Leu Ala
65                  70                  75                  80

Ile Ser Arg Leu Glu Ser Ser Ile Gly Ala Leu Gln Thr Val Val Asn
                85                  90                  95

Gly Leu Asp Ser Ser Val Thr Gln Leu Gly Ala Arg Val Gly Gln Leu
                100                 105                 110

Glu Thr Gly Leu Ala Asp Val Arg Val Asp His Asp Asn Leu Val Ala
            115                 120                 125

Arg Val Asp Thr Ala Glu Arg Asn Ile Gly Ser Leu Thr Thr Glu Leu
        130                 135                 140

Ser Thr Leu Thr Leu Arg Val Thr Ser Ile Gln Ala Asp Phe Glu Ser
145                 150                 155                 160

Arg Ile Ser Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
                180                 185                 190

Thr Leu Ser Gly Asn Asn Leu Ala Ile Arg Leu Pro Gly Asn Thr Gly
            195                 200                 205

Leu Asn Ile Gln Asn Gly Gly Leu Gln Phe Arg Phe Asn Thr Asp Gln
        210                 215                 220

Phe Gln Ile Val Asn Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
                260                 265                 270

Leu Ile Asp Ser Ser Thr Leu Glu Ile Asn Ser Ser Gly Gln Leu Thr
            275                 280                 285

Val Arg Ser Thr Ser Pro Asn Leu Arg Tyr Pro Ile Ala Asp Val Ser
        290                 295                 300
```

```
Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
            325                 330                 335

Val Asn Ser Asp Ile Phe Ile Val Asp Asp Tyr Ile His Ile Cys Leu
                340                 345                 350

Pro Ala Phe Asp Gly Phe Ser Ile Ala Asp Gly Gly Asp Leu Ser Leu
            355                 360                 365

Asn Phe Val Thr Gly Leu Leu Pro Pro Leu Leu Thr Gly Asp Thr Glu
        370                 375                 380

Pro Ala Phe His Asn Asp Val Val Thr Tyr Gly Ala Gln Thr Val Ala
385                 390                 395                 400

Ile Gly Leu Ser Ser Gly Gly Ala Pro Gln Tyr Met Ser Lys Asn Leu
                405                 410                 415

Trp Val Glu Gln Trp Gln Asp Gly Val Leu Arg Leu Arg Val Glu Gly
            420                 425                 430

Gly Gly Ser Ile Thr His Ser Asn Ser Lys Trp Pro Ala Met Thr Val
        435                 440                 445

Ser Tyr Pro Arg Ser Phe Thr
        450                 455

<210> SEQ ID NO 2
<211> LENGTH: 462
<212> TYPE: PRT
<213> ORGANISM: Mammalian orthoreovirus 2

<400> SEQUENCE: 2

Met Ser Asp Leu Val Gln Leu Ile Arg Arg Glu Ile Leu Leu Leu Thr
1               5                   10                  15

Gly Asn Gly Glu Ser Ala Asn Ser Lys His Glu Ile Glu Glu Ile Lys
            20                  25                  30

Lys Gln Ile Lys Asp Ile Ser Ala Asp Val Asn Arg Ile Ser Asn Ile
        35                  40                  45

Val Asp Ser Ile Gln Gly Gln Leu Gly Gly Leu Ser Val Arg Val Ser
    50                  55                  60

Ala Ile Glu Ser Gly Val Ser Glu Asn Gly Asn Arg Ile Asp Arg Leu
65                  70                  75                  80

Glu Arg Asp Val Ser Gly Ile Ser Ala Ser Val Ser Gly Ile Asp Ser
                85                  90                  95

Arg Leu Ser Glu Leu Gly Asp Arg Val Asn Val Ala Glu Gln Arg Ile
            100                 105                 110

Gly Gln Leu Asp Thr Val Thr Asp Asn Leu Leu Glu Arg Ala Ser Arg
        115                 120                 125

Leu Glu Thr Glu Val Ser Ala Ile Thr Asn Asp Leu Gly Ser Leu Asn
    130                 135                 140

Thr Arg Val Thr Thr Glu Leu Asn Asp Val Arg Gln Thr Ile Ala Ala
145                 150                 155                 160

Ile Asp Thr Arg Leu Thr Thr Leu Glu Thr Asp Ala Val Thr Ser Val
                165                 170                 175

Gly Gln Gly Leu Gln Lys Thr Gly Asn Ser Ile Lys Val Ile Val Gly
            180                 185                 190

Thr Gly Met Trp Phe Asp Arg Asn Asn Val Leu Gln Leu Phe Val Ser
        195                 200                 205

Asn Gln Gln Lys Gly Leu Gly Phe Ile Asp Asn Gly Met Val Val Lys
```

```
            210                 215                 220
Ile Asp Thr Gln Tyr Phe Ser Phe Asp Ser Asn Gly Asn Ile Thr Leu
225                 230                 235                 240

Asn Asn Asn Ile Ser Gly Leu Pro Ala Arg Thr Gly Ser Leu Glu Ala
                245                 250                 255

Ser Arg Ile Asp Val Val Ala Pro Pro Leu Val Ile Gln Ser Thr Gly
                    260                 265                 270

Ser Thr Arg Leu Leu Arg Leu Met Tyr Glu Ala Val Asp Phe Val Val
            275                 280                 285

Thr Asn Asn Val Leu Thr Leu Arg Asn Arg Ser Val Thr Pro Thr Phe
        290                 295                 300

Lys Phe Pro Leu Glu Leu Asn Ser Ala Asp Asn Ser Val Ser Ile His
305                 310                 315                 320

Arg Asn Tyr Arg Ile Arg Leu Gly Gln Trp Ser Gly Gln Leu Glu Tyr
                325                 330                 335

His Thr Pro Ser Leu Arg Trp Asn Ala Pro Val Thr Val Asn Leu Met
                    340                 345                 350

Arg Val Asp Asp Trp Leu Ile Leu Ser Phe Thr Arg Phe Ser Thr Ser
            355                 360                 365

Gly Ile Leu Ala Ser Gly Lys Phe Val Leu Asn Phe Val Thr Gly Leu
        370                 375                 380

Ser Pro Gly Trp Ala Thr Gly Ser Thr Glu Pro Ser Thr Thr Thr Asn
385                 390                 395                 400

Pro Leu Ser Thr Thr Phe Ala Ala Ile Gln Phe Ile Asn Gly Ser Ser
                405                 410                 415

Arg Val Asp Ala Phe Arg Ile Leu Gly Val Ala Glu Trp Asn Ala Gly
                    420                 425                 430

Glu Leu Glu Ile Thr Asn Tyr Gly Gly Thr Tyr Thr Ala His Thr Asn
            435                 440                 445

Val Asp Trp Ala Pro Met Thr Ile Met Tyr Pro Cys Leu Gly
        450                 455                 460
```

<210> SEQ ID NO 3
<211> LENGTH: 470
<212> TYPE: PRT
<213> ORGANISM: Mammalian orthoreovirus 2

<400> SEQUENCE: 3

```
Met Asp Ala Ser Leu Ile Thr Glu Ile Arg Lys Ile Val Leu Gln Leu
1               5                   10                  15

Ser Val Ser Ser Asn Gly Ser Gln Ser Lys Glu Ile Glu Glu Ile Lys
                20                  25                  30

Lys Gln Val Gln Val Asn Val Asp Asp Ile Arg Ala Ala Asn Ile Lys
            35                  40                  45

Leu Asp Gly Leu Gly Arg Gln Ile Ala Asp Ile Ser Asn Ser Ile Ser
        50                  55                  60

Thr Ile Glu Ser Arg Leu Gly Glu Met Asp Asn Arg Leu Val Gly Ile
65                  70                  75                  80

Ser Ser Gln Val Thr Gln Leu Ser Asn Ser Val Ser Gln Asn Thr Gln
                85                  90                  95

Ser Ile Ser Ser Leu Gly Asp Arg Ile Asn Ala Val Glu Pro Arg Val
            100                 105                 110

Asp Ser Leu Asp Thr Val Thr Ser Asn Leu Thr Gly Arg Thr Ser Thr
        115                 120                 125
```

-continued

```
Leu Glu Ala Asp Val Gly Ser Leu Arg Thr Glu Leu Ala Ala Leu Thr
    130                 135                 140
Thr Arg Val Thr Thr Glu Val Thr Arg Leu Asp Gly Leu Ile Asn Ser
145                 150                 155                 160
Gly Gln Asn Ser Ile Gly Glu Leu Ser Thr Arg Leu Ser Asn Val Glu
                165                 170                 175
Thr Ser Met Val Thr Thr Ala Gly Arg Gly Leu Gln Lys Asn Gly Asn
            180                 185                 190
Thr Leu Asn Val Ile Val Gly Asn Gly Met Trp Phe Asn Ser Ser Asn
        195                 200                 205
Gln Leu Gln Leu Asp Leu Ser Gly Gln Ser Lys Gly Val Gly Phe Val
    210                 215                 220
Gly Thr Gly Met Val Val Lys Ile Asp Thr Asn Tyr Phe Ala Tyr Asn
225                 230                 235                 240
Ser Asn Gly Glu Ile Thr Leu Val Ser Gln Ile Asn Glu Leu Pro Ser
                245                 250                 255
Arg Val Ser Thr Leu Glu Ser Ala Lys Ile Asp Ser Val Leu Pro Pro
            260                 265                 270
Leu Thr Val Arg Glu Ala Ser Gly Val Arg Thr Leu Ser Phe Gly Tyr
        275                 280                 285
Asp Thr Ser Asp Phe Thr Ile Ile Asn Ser Val Leu Ser Leu Arg Ser
    290                 295                 300
Arg Leu Thr Leu Pro Thr Tyr Arg Tyr Pro Leu Glu Leu Asp Thr Ala
305                 310                 315                 320
Asn Asn Arg Val Gln Val Ala Asp Arg Phe Gly Met Arg Thr Gly Thr
                325                 330                 335
Trp Thr Gly Gln Leu Gln Tyr Gln His Pro Gln Leu Ser Trp Arg Ala
            340                 345                 350
Asn Val Thr Leu Asn Leu Met Lys Val Asp Asp Trp Leu Val Leu Ser
        355                 360                 365
Phe Ser Gln Met Thr Thr Asn Ser Ile Met Ala Asp Gly Lys Phe Val
    370                 375                 380
Ile Asn Phe Val Ser Gly Leu Ser Ser Gly Trp Gln Thr Gly Asp Thr
385                 390                 395                 400
Glu Pro Ser Ser Thr Ile Asp Pro Trp Ser Thr Thr Phe Ala Ala Val
                405                 410                 415
Gln Phe Leu Asn Asn Gly Gln Arg Ile Asp Ala Phe Arg Ile Met Gly
            420                 425                 430
Val Ser Glu Trp Thr Asp Gly Glu Leu Glu Ile Lys Asn Tyr Gly Gly
        435                 440                 445
Thr Tyr Thr Gly His Thr Gln Val Tyr Trp Ala Pro Trp Thr Ile Met
    450                 455                 460
Tyr Pro Cys Asn Val Arg
465                 470
```

ATTENUATED REOVIRUSES FOR SELECTION OF CELL POPULATIONS

This application claims benefit of priority to U.S. Provisional Application Ser. No. 60/906,710, filed Mar. 13, 2007, the entire contents of which are hereby incorporated by reference.

This application is related to International Patent Application No. PCT/US2006/029881, filed Jul. 31, 2006, U.S. Provisional Application Ser. No. 60/704,604, filed Aug. 5, 2006, and U.S. Provisional Application Ser. No. 60/906,706, filed Mar. 13, 2007, the entire contents of which are incorporated herein by reference.

The government may own rights in the present invention pursuant to grant numbers 73-0520 (CIHR) and 73-2965 (ACB) from The Canadian Institutes of Health Research and The Alberta Cancer Board.

BACKGROUND OF THE INVENTION

1. Field of the Invention

The present invention relates generally to the fields of virology, molecular biology and medicine. More particularly, it concerns methods involving attenuated reoviruses for screening or selectively killing certain (e.g., cancerous) sub-populations of cells in vitro or from a larger mixed cell population.

2. Description of Related Art

Reovirus (Respiratory Enteric Orphan virus) is a ubiquitous, non-enveloped virus containing 10 segments of double-stranded RNA as its genome, with human infections that are generally mild, restricted to the upper respiratory and gastrointestinal tracts and often asymptomatic, in immune functional hosts (Tyler, 2001). Attempts to reverse engineer reoviruses have been largely unsuccessful due to several factors, including the double-stranded RNA genome of reoviruses. Reoviral particles lacking σ1 have been understood to be non-infectious (Larson et al., 1994).

Importantly, reovirus has been recognized for many years as displaying striking cytocidal activity when it infects certain types of transformed cells (Duncan et al., 1978; Hashiro et al., 1977). Replication-competent oncolytic viruses provide an attractive anti-cancer therapeutic approach. These oncolytic viruses have two principal advantages. Firstly, unlike conventional chemotherapy and radiotherapy, they specifically target cancer cells because of their restricted ability to replicate in normal cells. Secondly, as compared to replication-incompetent vectors, they can propagate from initially infected cancer cells to surrounding cancer cells, thereby achieving a large volume of distribution and potent anti-cancer effects.

Exposure to wild-type (wt) reoviruses, although often asymptomatic in healthy individuals, can nonetheless present a substantial and potentially very serious risk to immunocompromised individuals, limiting the clinical potential of reoviral therapies in patients such as cancer patients who might otherwise benefit from such a therapy. The underlying basis for reoviral oncolytic activity remained unknown until it was shown that transformed cells containing oncogenic Ras-signaling pathways were preferentially susceptible to reovirus infection (type 3 Dearing strain) in vitro and in vivo (Coffey et al., 1998; Strong et al., 1998; Norman et al., 2004). As Ras gene mutations are frequently observed in various types of human cancers (Duursma et al., 2003), these findings have led to the current use of reoviral therapy in clinical trials (Norman et al., 2005). In immune compromised hosts such as newborn and SCID (severe combined immunodeficiency) animals, however, the wt reovirus exerts significant viral pathogenesis especially in neural tissue and cardiac muscle tissue (Sabin, 1959; Weiner et al., 1977; Baty et al., 1993; Loken et al., 2004). In some cases, even in immune-competent hosts including humans, wt reovirus has been associated with viral pathogenesis (Terheggen et al., 2003, Hirasawa et al., 2003). Therefore, especially in immune-compromised or very young hosts, wt reovirus does not always act in a benign manner. For example, in immunocompromised hosts such as very young or immunodeficient adult animals, this virus also has been shown to infect some healthy tissues such as heart, liver, pancreas and neural structures. This concern may further apply to cancer patients treated with extensive radio/chemotherapy as they can be subject to immunosuppression. Thus, there is a clear need to develop a less virulent reovirus for viral oncolytic therapy.

Further, wt reoviruses in many instances possess undesirable virulence and infectivity which limit their potential use in vitro. Specifically, exposure of a cell culture (e.g., a bone marrow transplant taken from a cancer patient) to wt reoviruses may result in the undesirable side effect of killing cells such as stem cells which would be needed for a purpose such as repopulating the immune system of a cancer patient. Thus, the increased virulence of WT reoviruses present significant limitations for the clinical potential of in vitro applications involving exposure of cells to reoviruses. Certain methods relating to the exposure of cellular populations to wt reoviruses have been described (e.g., U.S. Pat. No. 6,994,858, U.S. Patent Publication 2004/0109878, U.S. Patent Publication 2002/0037543, U.S. Patent Publication 2006/0029598, U.S. Patent Publication 2005/0026289, U.S. Patent Publication 2002/0006398, U.S. Patent Publication 2001/0048919 which are incorporated by reference in their entirety without disclaimer); however these methods do not resolve the above-mentioned limitations involving the use of WT reoviruses. Clearly, there exists a need for improved methods for selective killing or purging of cellular sub-populations (e.g., cancerous cells) from a mixed cellular population while limiting damage to necessary or beneficial cells (e.g., stem cells, hematopoietic stem cells).

SUMMARY OF THE INVENTION

The present invention overcomes limitations in the prior art by providing methods for the screening or purging of cellular sub-populations (e.g., cancerous cells) from a mixed cellular population in vitro using attenuated reoviruses. In certain embodiments, an attenuated reovirus lacking a wild-type S1 gene may be exposed to a mixed cellular composition; the decreased virulence of the attenuated reovirus can then result in killing of cancerous or neoplastic cells with a reduced toxicity to healthy cells such as stem cells or hematopoietic cells. In various embodiments, the mixed cellular composition may be obtained from various sources such as an autologous or allogenic tissue sample (e.g., blood, bone marrow, cultured stem cells such as adult stem cells, embryonic stem cells, partially differentiated precursor cells, etc.).

An aspect of the present invention relates to a method to kill or remove neoplastic cells from a cellular composition suspected of containing such neoplastic cells comprising contacting the cells with an attenuated reovirus under conditions which result in oncolysis or killing of one or more of the neoplastic cells. The attenuated reovirus may express a defective σ1 capsid protein, an undetectable σ1 capsid protein, or no σ1 capsid protein. The attenuated reovirus may lack a wild-type reovirus S1 gene. The attenuated reovirus may lack a wild-type reovirus S4 gene. The attenuated reovirus may have a heritable mutant reovirus S1 gene and/or a heritable mutant reovirus S4 gene. In certain embodiments, the attenuated reovirus is a mammalian reovirus, such as a human reovirus. In certain embodiments, the human reovirus is the AV reovirus.

The cellular composition may comprise stem cells, such as embryonic stem cells. In certain embodiments, the embryonic stem cells are derived from cord blood or placenta. The stem cells may be adult stem cells, hematopoietic stem cells, or human hematopoietic stem cells. The cellular composition may be harvested from bone marrow or blood, such as mobilized peripheral blood. The method may further comprise contacting the attenuated reovirus-treated cellular composition with an anti-reovirus antibody, a peptidyl fluoromethyl ketone (e.g., Z-FA-FMK), an RNA-directed RNA polymerase inhibitor, or an antiviral agent. The method may further comprise removing one or more attenuated reovirus from the cellular composition via washing, centrifugation, or fluorescence activated cell sorting.

The attenuated reovirus-treated cellular composition may be transplanted or implanted into a recipient. In certain embodiments, the cellular composition comprises bone marrow. The recipient may be a human. In certain embodiments, the recipient has received or will receive a cancer therapy, a chemotherapy, or a radiation therapy. The recipient may be immunocompromised. The recipient may be immunocompromised due to a cancer therapy, a chemotherapy, a radiation therapy, or HIV. The transplantation may be autologous or allogenic. The cellular composition may comprise hematopoietic stem cells.

In certain embodiments, the method comprises a method for reducing a risk of recurrence of cancer or tumors in a human patient due to transplantation of the cellular composition, wherein the cellular composition comprises hematopoietic stem cells; wherein the cellular composition is obtained from the human patient; and wherein the attenuated reovirus-treated composition is implanted into the patient. The cellular composition may be a mixed cellular composition.

Another aspect of the present invention relates to a method to kill or remove neoplastic cells from a cellular composition suspected of containing such neoplastic cells comprising contacting the cells ex vivo with an attenuated reovirus under conditions which result in oncolysis of one or more of the neoplastic cells.

Yet another aspect of the present invention relates to a cellular composition prepared according to the methods of the present invention.

As used herein, "neoplastic cells," also known as "cells with a proliferative disorder," refer to cells which proliferate without the normal growth inhibition properties. A new growth comprising neoplastic cells is a neoplasm or tumor. A neoplasm is an abnormal tissue growth, generally forming a distinct mass, that grows by cellular proliferation more rapidly than normal tissue growth. Neoplasms may show partial or total lack of structural organization and functional coordination with normal tissue. As used herein, a neoplasm is intended to encompass hematopoietic neoplasms as well as solid neoplasms.

A neoplasm may be benign (benign tumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to, neurofibromatosis.

As used herein, "immunocompromised" refers to a subject (e.g., a non-human animal, a mammal, a human patient) with an immune system rendered deficient relative to a normal subject by, for example, a genetic mutation or disorder (e.g., a mouse bred to possess a deficient immune system), an immunodeficiency disorder, a disease (e.g., HIV), administration of an immunosuppressive agent (e.g., a chemotherapeutic), or exposure to radiation. Examples of immunocompromised subjects include mammals or human patients suffering from a viral infection such as AIDS, CMV, or influenza. Immunocompromised subjects also include a patient or subject receiving a chemotherapy and/or radiotherapy (e.g., to treat a cancer), transplant patients receiving anti-rejection agents and patients that have been exposed to a sufficient level of a toxic chemical, metal and radiation exposure.

As used herein, "cellular composition" means a composition comprising cells. The composition may contain non-cellular matter. For example, whole blood is a cellular composition which contains plasma, platelets, hormones and other non-cellular matter in addition to cells such as erythrocytes and leukocytes. A cellular composition may contain cells of various types, origin or organization. For example, tissues and organs which contain different cell types arranged in defined structures are considered cellular compositions. Cellular compositions which contain more than one cell type are referred to as "mixed cellular compositions."

The term "isolated" means that the material is removed from its original environment (e.g., the natural environment if it is naturally occurring). For example, a naturally occurring nucleic acid or polypeptide present in an intact virus or in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

As used herein, a "peptidyl fluoromethylketone" (PFMK) is a fluoromethylketone-containing compound that contains two or more amino acids and reduces or inhibits viral replication by about 50%, about 55%, about 60%, about 65%, about 70%, about 75%, about 80%, about 85%, about 90%, about 95%, about 99%, about 100%, or any value or range in between. The amino acid may be any natural amino acid, any unnatural amino acid, or any combination thereof, as known by those of skill in the art. In certain aspects, a PFMK may be chemically modified and still retain the desired effects of the PFMK compound prior to the chemical modification. Such modified PFMKs may involve the addition, removal, or substitution of one or more chemical moieties on the parent PFMK molecule. Non-limiting examples of the types modifications that can be made to the compounds and structures disclosed herein include the addition or removal of peptide moiety, or lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic structure, heteroatoms such as N, S, or O can be substituted into the structure instead of a carbon atom.

A variety of amino protecting groups may be appended to the N-terminus of a PFMK. Such protecting groups are well-known in the art, and non-limiting examples include a benzyloxycarbonyl (Z or Cbz) group, a t-butoxycarbonyl (Boc) group and an N-morpholineurea group. Other such groups are listed in Greene and Wuts, 1999, incorporated herein in its entirety. Such protecting groups may be chemically modified as described above.

Yet other modifications to a PFMK may include the addition of substituents that target the resultant PFMK to a particular cellular compartment, such as an endosome or a lysosome. Such substituents are well-known in the art. Non-limiting examples of cellular compartment-targeting substituents include cyclodextrin and galactosyl carbohydrate groups. Such substituents may localize enhancement in concentration of the PFMK at the site of its putative activity, allowing for lower concentrations of the PFMK to be administered. Such substituents may also provide enhanced solubility, persistance and/or stability in vivo and/or in vitro. The present invention specifically contemplates PFMKs that comprise cellular compartment-targeting substituents.

Exemplary PFMKs include N-benzyloxycarbonyl-Phe-Ala-fluoromethylketone (Z-FA-FMK), Mu-FhF-FMK (N-morpholineurea-phenylalanyl-homophenylalanyl-fluoromethylketone) and Z-VAD-FMK (Z-Val-Ala-Asp-fluoromethylketone).

In certain aspects, a PFMK may be characterized as follows, wherein R represents a di-, tri-, tetra-, penta-, or hexa-peptide:

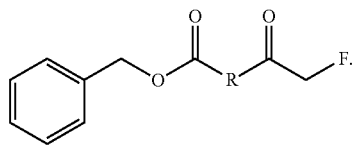

The term "effective," as that term is used in the specification and/or claims, means adequate to accomplish a desired, expected, or intended result.

The terms "contacted" and "exposed," when applied to a cell, tissue or organism, are used herein to describe the process by which a PFMK compound, such as a cathepsin inhibitor, e.g., Z-FA-FMK, Mu-FhF-FMK, is delivered to a target cell, tissue or organism or is placed in direct juxtaposition with the target cell, tissue or organism.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A, At 48 hrs post-infection, viral cytopathic effects were photographed. Extensive cytopathic effects were observed upon wt reovirus infection. FIG. 2B, Cell lysates were then prepared at 48 hrs post-infection and viral proteins (λ, µ, σ) were detected by western blotting using reovirus antiserum. At 48 hrs post-infection, cells were fixed/permeablized for analysis by FACS using reovirus antiserum and secondary FITC antiserum.

FIG. 3A, SCID mice received a single implantation of murine R1 ESCs. 12 days after implantation, teratomas were intratumorally injected with reoviruses [wt Reo (wild-type reovirus, $10^7$ PFU per mouse), circle: n=5, AV Reo (AV reovirus, $10^7$ PFU per mouse), rectangle: n=5, D Reo (Dead, UV-inactivated reovirus), triangle: n=5] and teratoma growth was followed 21-70 days post-infection. FIG. 3B, SCID mice received a single implantation of murine MES1 ESCs. 12-15 days after implantation, teratomas were intratumorally injected with reoviruses or PBS [wt Reo (wild-type reovirus, 107 PFU per mouse), circle: n=3, AV Reo (AV reovirus, 107 PFU per mouse), rectangle: n=3, PBS, triangle: n=3] and teratoma growth was followed up to 31-46 days post-infection. wt reovirus treated mice were sacrificed at 18-19 days post-infection due to viral myocarditis caused by wt reovirus. FIG. 3C, Photographs of representative R1 teratomas were taken 21 days after implantation.

Figure 1:
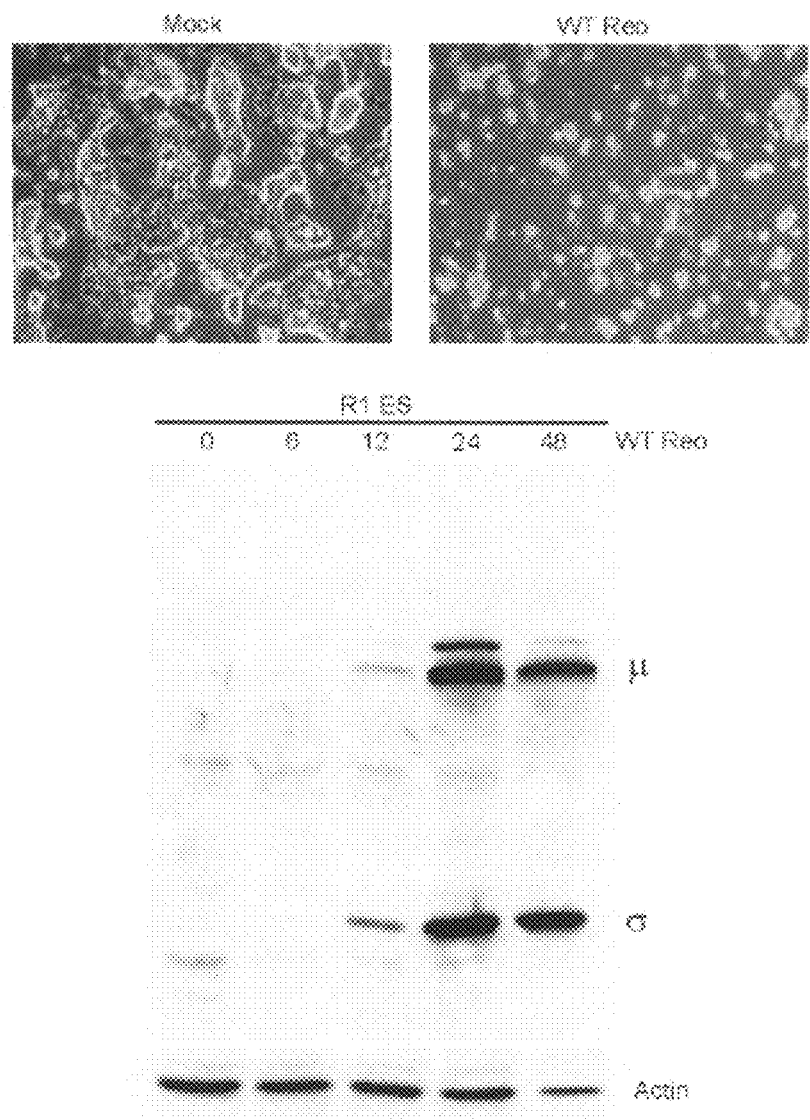
FIG. 1: WT reovirus induced viral cytopathogenicity on embryonic stem cells. Undifferentiated murine embryonic stem cells (R1) grown in the presence of leukemia inhibitory factor (LIF) were infected with wt reovirus at multiplicity of infection (MOI) of 20. At 48 hrs post-infection, viral cytopathic effects were photographed. Cell lysates were prepared at the indicated time points (hrs) and viral proteins (µ, σ) were detected by western blotting using reovirus-antiserum. R1 ESC: R1 embryonic stem cells, Mock: mock infection.

The patent or application file contains at least one drawing executed in color. Copies of this patent or patent application publication with color drawing(s) will be provided by the Office upon request and payment of the necessary fee.

DESCRIPTION OF ILLUSTRATIVE EMBODIMENTS

The present invention relates, in certain embodiments, to an attenuated reovirus having desirable properties for use as an oncolytic agent ex vivo or in vitro, thereby providing unexpected advantages over naturally-occurring wild-type reoviruses. The attenuated reovirus used in the below examples and disclosed herein comprises an infectious, replication-competent reovirus virion that lacks a detectable reovirus σ1 capsid protein by virtue of the genome of such reovirus lacking a wild-type reovirus S1 gene. As such, the attenuated reovirus derives from the surprising observation that a mutated reovirus which lacks a detectable reovirus σ1 capsid protein unexpectedly retains the ability to productively infect a target tumor cell while desirably avoiding cytopathic effects on non-malignant cells. As noted above, prior to the instant disclosure, reoviral particles that lacked σ1 had been understood to be non-infectious (Larson et al., 1994).

The present invention provides methods for the screening or purging of cellular subpopulations (e.g., cancerous cells) from a mixed cellular population in vitro using an attenuated reovirus. In certain embodiments, an attenuated reovirus lacking a wild-type S1 gene may be exposed to a mixed cellular composition; the decreased virulence of the attenuated reovirus can then result in killing of cancerous or neoplastic cells with a reduced toxicity to healthy cells such as stem cells or hematopoietic cells. In various embodiments, the mixed cellular composition may be obtained from various sources such as an autologous or allogenic tissue sample (e.g., blood, bone marrow, cultured stem cells such as embryonic stem cells, partially differentiated precursor cells, etc.).

As shown in the below examples, attenuated reoviruses demonstrate significant safety for use with stem cells such as adult or embryonic stem cells, including hematopoietic stem cells. In contrast to wild-type (wt) reovirus, evidence that the attenuated AV reovirus did not inhibit growth of a teratoma in a mouse model in the below examples, combined with evidence of the anti-neoplastic effects of this attenuated reovirus, indicates that the AV reovirus may be administered to a cell population comprising healthy stem cells such as hematopoietic cells and selectively kill or purge neoplastic cells from the composition while resulting in little or no damage or toxicity to the healthy stem cells. The reduced cytopathogenicity of attenuated reovirus (e.g., the AV reovirus) towards healthy stem cells allows for safer in vitro killing of cancerous cells from a mixed cellular composition that comprises stem cells (e.g., a bone marrow transplant comprising hematopoietic stem cells).

I. Attenuated Reoviruses

The reoviruses (Reoviridae) comprise a family of naturally-occurring, non-enveloped viruses having a double-stranded RNA (dsRNA) genome that is divided into ten segments and enclosed by two concentric icosahedral protein capsids. Infectious mammalian reovirus virions of various tropisms occur as particles of approximately 85 nm in diameter. The virion outer capsid includes several distinct protein species, among them sigma-1 (σ1, 50 kDa) which mediates viral attachment to host cell surfaces (Lee et al., 1981; Duncan et al., 1991; Nagata et al., 1987; Turner et al., 1992) via discrete carbohydrate-binding (Chappell et al., 1997; Chappell et al., 2000; Connolly et al., 2001) and virion-anchoring (Mah et al., 1990; Fernandes et al., 1994; Lee et al., 1994) domains. σ1 is a product of the bicistronic reoviral S1 gene, which also encodes a non-structural protein designated σ1s using a distinct but overlapping reading frame (Ernst et al., 1985; Jacobs et al., 1985; Sarkar et al., 1985). Reoviral particles that lack GI have been reported to be non-infectious (Larson et al., 1994). The reoviral S1 gene has been believed to play a significant role in determining reoviral pathogenesis (Haller et al., 1995; Wilson et al., 1994; Kaye et al., 1986; Weiner et al., 1980).

The herein described attenuated reovirus lacks a detectable σ1 capsid protein yet is, unexpectedly, infectious. σ1 has been implicated in reoviral binding and attachment to cells via cell surface sialic acid residues in an initial step of viral replicative infection (Lee et al., 1981; Duncan et al., 1991; Nagata et al., 1987; Turner et al., 1992; Chappell et al., 1997; Chappell et al., 2000; Connolly et al., 2001). Despite lacking detectable σ1, the attenuated reovirus described herein is capable of host cell entry and cytolytic viral replication. Additionally, the attenuated reovirus exhibits the surprising property of inducing a decreased (i.e., reduced with statistical significance) level of one or more cytopathic effects toward a non-malignant cell relative to the level of the cytopathic effect that is exhibited toward the non-malignant cell by a naturally occurring, non-attenuated reovirus. Accordingly and as described in greater detail below, the attenuated reovirus provided herein offers improvements over reoviruses of the prior art, including suitability for use as an oncolytic agent without undesirable side-effects such as tropism for, and cytolysis of, normal (e.g., non-malignant) cells. Specifically, this attenuated reovirus may be used in vitro for the selective killing of cancerous or neoplastic cells.

In certain embodiments, an attenuated reovirus as described in U.S. Application 60/704,604, filed Aug. 5, 2006, and International Patent Application No. PCT/US2006/029881, filed Jul. 31, 2006, which are incorporated by reference herein in its entirety without disclaimer, may be used with the present invention. In certain embodiments, the attenuated reovirus may lack a wild-type reovirus S1 gene. The attenuated reovirus may possess a S1 gene which produces a reduced and/or undetectable amount of the S1 gene product (σ1) or a truncated, mutated, and/or dysfunctional σ1. An attenuated reovirus may have a S1 gene that contains one or more mutations, as compared to a wild-type S1 gene, wherein the mutation is a nucleotide substitution, a nucleotide deletion or a nucleotide insertion.

"Attenuated" reoviruses described herein include reoviruses that exhibit altered (i.e., increased or decreased in a statistically significant manner) infective, replicative and/or lytic properties toward or in a host cell, relative to levels of one or more such properties that are exhibited by known, naturally occurring or wild-type reoviruses. In certain embodiments, the attenuated reovirus will exhibit decreased infectivity, replicative ability and/or lytic potential, relative to a wild-type reovirus. Examples of such altered properties by which one may discern an attenuated reovirus as presently disclosed include various manifestations of viral cytopathic effects, for instance, the multiplicity of infection (MOI, the average number of virions that infect each cell) required for productive infection of a given host cell, the degree of host cell cytolysis induced by viral infection (further including apoptosis and/or necrosis), the titer of viruses released from a productively infected host cell following cytolytic viral replication, and other parameters by which those familiar with the art can determine viral activities toward host cells. Other indicia of cytopathic effects include altered host cell morphology, altered cell adhesion (to substrates such as extracellular matrix proteins or semisolid growth media, or to other cells), altered expression levels of one or more cellular genes, altered ability of host cells to replicate, and/or other alterations in cellular metabolic activity.

A. Mutant Reovirus S1 and S4 Genes

Considering that the S1 gene segment of reovirus is strongly associated with reoviral virulence (Weiner et al., 1977; Weiner et al., 1980; Mann et al., 2002), the inventors have surprisingly isolated an S1 attenuated reovirus ("AV reovirus") from a persistent reovirus infection of cultured cells (Kim et al., 2006). The attenuated reovirus strain displays significantly reduced viral pathogenesis in an immune-deficient animal model without compromising its viral oncolytic activity in vivo. Because wt reovirus is known to adversely affect the development of rat and murine embryos by retarding development and inhibiting blastocytst formation (Priscott, 1983; Heggie et al., 1979), the inventors further evaluated the pathogenicity of AV reovirus on stem cells. Thus, the inventors compared the pathogenicity of wt and AV reovirus on embryonic stem cells (ESCs). As shown in the below examples, wt reovirus readily infects ESCs in vitro and significantly suppresses stem cell development in a teratoma model, whereas AV reovirus minimally infects ESCs in vitro and does not affect stem cell development in a teratoma model.

In various embodiments, the attenuated reovirus may comprise one or more additional mutations. For example, in certain further embodiments, the attenuated reovirus may lack a wt reovirus S4 gene. The reovirus wt S4 gene encodes a reovirus capsid σ3 polypeptide involved in virion processing during reoviral replicative infection of a host cell (e.g., Ahmed et al., 1982; Giantini et al., 1984).

The attenuated reovirus may comprise a replication-competent reovirus virion. Further, an attenuated reovirus may have a heritable mutation (e.g., substitution, insertion deletion) in the S1 gene and/or the S4 gene.

The wt reovirus S1 gene is known to those of skill in the art. For example, wt S1 gene sequences include the S1 gene sequences identified in predominant forms of naturally-occurring reoviruses isolated from respiratory or enteric tissues of infected subjects, or consensus sequences derived from such sequences. S1 gene sequences for a number of reoviruses, including the human reoviruses, have been determined, (e.g., Genbank Accession numbers for human reovirus S1 gene sequences: human type 3 reovirus S1: X01161; human type 2 reovirus S1: M35964; human type 1 reovirus S1: M35963) including polynucleotide sequences encoding σ1 proteins as well as the amino acid sequences of the encoded σ1 proteins themselves. (e.g., Genbank Accession numbers for major human reovirus serotype S1 gene sequences: human type 1 reovirus strain Lang (T1L) Acc. No. M35963; human type 2 reovirus strain Jones (T2J) Acc. No. M35964; human type 3 reovirus strain Dearing (T3D) Acc. No. X01161; human type 3 reovirus strain Abney (T3A) Acc. No. L37677.

According to certain embodiments, there is provided an attenuated reovirus comprising a reovirus genome that lacks a wild-type reovirus S1 gene, or that comprises a mutated reovirus S1 gene that is incapable of encoding a reovirus σ1 capsid protein that has an amino acid sequence that is greater than 10%, 20%, 40%, 50%, 70%, 90%, or 95% identical to the amino acid sequence set forth in SEQ ID NOS:1-3 (Genbank Accession numbers for human reovirus S1 gene sequences: human type 3 reovirus S1: X01161; human type 2 reovirus S1: M35964; human type 1 reovirus S1: M35963). Methodologies for determining whether a mutated S1 gene is present by sequencing a reovirus S1 gene will be apparent from the present disclosure and as known in the art, according to techniques described, for example, in Ausubel et al. (1989); Ausubel et al. (1993); Sambrook et al. (1989); Maniatis et al. (1982); Glover (1985); Hames and Higgins (1985); and elsewhere. A mutated S1 gene thus refers to an S1 gene having a polynucleotide sequence that differs at one or a plurality of nucleotide sequence positions from the nucleotide sequence of a corresponding S1 wt or consensus sequence by one or more of a nucleotide substitution, a nucleotide insertion, and a nucleotide deletion, as can be readily determined.

Additionally or alternatively, polynucleotide sequences of reoviral S1 genes, or amino acid sequences of reoviral S1 polypeptides, can be compared for purposes of determining whether a mutated S1 gene (or its product) may be present. As known in the art "similarity" between two polypeptides is determined by comparing the amino acid sequences and conserved amino acid substitutions thereto of a first polypeptide to the sequence of a second polypeptide. As used herein, "% identity" refers to the percentage of identical amino acids situated at corresponding amino acid residue positions when two or more polypeptide are aligned and their sequences analyzed using an appropriate sequence analysis tool, such as the gapped BLAST algorithm (e.g., Altschul et al., 1997) which weights sequence gaps and sequence mismatches according to the default weightings provided by the National Institutes of Health/NCBI database (Bethesda, Md.; see the world wide web address ncbi.nlm.nih.gov/cgi-bin/BLAST/nph-newblast), or with other similar tools (e.g., MEGALIGN™, GENEWORKS™, Align or the BLAST algorithm (Altschul, 1991; Henikoff et al., 1992), which is available at the NCBI website (see the world wide web address ncbi.nlm.nih.gov/cgi-bin/BLAST>). Other sequence alignment algorithms, with which those having ordinary skill in the art will be familiar, may also be used.

The presence of nucleic acids which hybridize to σ1 encoding polynucleotide sequences, or their complements, can be determined, as will be readily apparent to those familiar with the art, if there is at least 70%, preferably 80-85%, more preferably at least 90%, and still more preferably at least 95%, 96%, 97%, 98% or 99% identity between the sequences. Certain embodiments particularly relate to nucleic acids which hybridize under stringent conditions to the σ1 encoding nucleic acids referred to herein. As used herein, the term "stringent conditions" means hybridization will occur only if there is at least 90-95% and preferably at least 97% identity between the sequences. The ability to detect presence or absence of nucleic acids which hybridize to σ1 encoding nucleic acids referred to herein may be used, in preferred embodiments, to determine whether a mutated reoviral S1 gene is incapable of encoding polypeptides which retain substantially the same biological function or activity as the wild-type reoviral σ1 polypeptides such as those described in the references cited herein.

As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed. Typically "high," "medium" and "low" stringency encompass the following conditions or equivalent conditions thereto: high stringency: 0.1×SSPE or SSC, 0.1% SDS, 65° C.; medium stringency: 0.2×SSPE or SSC, 0.1% SDS, 50° C.; and low stringency: 1.0×SSPE or SSC, 0.1% SDS, 50° C. As known to those having ordinary skill in the art, variations in stringency of hybridization conditions may be achieved by altering the time, temperature and/or concentration of the solutions used for prehybridization, hybridization and wash steps, and suitable conditions may also depend in part on the particular nucleotide sequences of the probe used, and of the blotted, proband nucleic acid sample. Accordingly, it will be appreciated that suitably stringent conditions can be readily selected without undue experimentation where a desired selectivity of the probe is identified, based on its ability to hybridize to one or more certain proband sequences while not hybridizing to certain other proband sequences.

According to certain embodiments there is provided an attenuated reovirus, comprising a replication-competent reovirus virion that comprises a heritable mutant reovirus S1 gene, the mutant S1 gene comprising one or a plurality of mutations in a reoviral σ1 encoding genomic sequence (e.g., SEQ ID NOS:1-3). Determination of the presence or absence of such a mutant (e.g., one or a plurality of nucleotide substitutions, insertions and/or deletions) is within the routine practice of the art as described herein. Similarly, a heritable mutant reovirus S1 gene refers to a mutated S1 gene (relative to a wild-type sequence such SEQ ID NOS:1-3) that is passed on from an infectious reovirus to progeny which result from productive infection of a host cell, wherein the presence of the heritable mutation in progeny virus can be determined based on the herein described mutated S1 gene, using established molecular biology procedures. Several mutations in a murine reoviral S1 gene sequence encoding a σ1 protein are disclosed by Hoyt et al. (2005) and according to certain embodiments of the invention described herein the mutations of Hoyt et al. are expressly excluded.

As described herein and known to the art, the reovirus outer capsid CY1 protein may be readily detected on the basis of its biochemical and/or immunochemical properties (e.g., Mah et al., 1990; Leone et al., 1991; Chappell et al., 1997), typically by employing one or more techniques including immunodetection (e.g., GI-specific immunoprecipitation, western immunoblot analysis, immunoaffinity chromatography, immunofluorescent staining, immunocytofluorimetry, electrophoresis of radiolabeled reovirus polypeptides, etc.), hemagglutination, and/or related methodologies. Accordingly these and other means for detecting a reoviral σ1 protein have been established, and in view of the teachings herein, those familiar with the art will appreciate what are art-accepted criteria and state-of-the-art sensitivity for detecting σ1 protein, such that a replication-competent reovirus virion that lacks a "detectable" reovirus σ1 capsid protein will be understood to include such a reovirus for which σ1 protein cannot be detected when currently conventional practices for determining σ1 protein, if present, are employed.

B. Production of Attenuated Reovirus

According to certain embodiments as disclosed herein, the attenuated reovirus may be derived from any reovirus, which refers to a member of the Family Reoviridae and includes reoviruses having a variety of tropisms and which may be obtained from a variety of sources (Tyler and Fields, 1996). In certain embodiments, mammalian reoviruses are preferred, and in certain further embodiments human reoviruses are particularly preferred as the starting point for the derivation of an attenuated reovirus as described herein, although the invention is not intended to be so limited, and based on the present disclosure the skilled artisan will recognize situations where any particular reovirus may be desirable for such purposes. In certain embodiments, the attenuated reovirus may be derived from human reoviruses, for example, human Type 3 (Dearing), Type 1 (Lang), Type 2 (Jones), or Type 3 (Abney) reoviruses, while in certain other embodiments (e.g., for use in animal models having relevance to human diseases, or for veterinary applications) the attenuated reovirus may be derived from one or more reoviruses displaying tropisms toward cells of other mammalian species, including non-human primates (e.g., chimpanzee, gorilla, macaque, monkey, etc.), rodents (e.g., mice, rats, gerbils, hamsters, rabbits, guinea pigs, etc.), dogs, cats, common livestock (e.g., bovine, equine, porcine, caprine), etc., or alternatively, reoviruses having distinct tropisms (e.g., avian reoviruses) may be used.

As described herein, certain embodiments relate to attenuated reoviruses that are recovered following persistent infection regimens in vitro, but attenuated reoviruses are also contemplated that may be derived according to other methodologies, including persistent infection regimens in vivo, generation and identification of σ1-deficient and/or σ1-defective mutants (and in certain embodiments also including, additionally or alternatively, generation and identification of σ3-deficient and/or σ3-defective mutants) by molecular biological approaches, and also including isolation of naturally occurring σ1-deficient and/or σ1-defective mutants and/or σ3 mutants, and/or artificial induction of such σ1 (and/or (σ3) mutants by chemical, physical and/or genetic techniques (e.g., assortative recombination of reoviral genes in a productively infected host cell).

Further, the inventors anticipate that mutations resulting in a desirable attenuation phenotype may be observed in other genes that affect viral infectivity, replicative or packaging ability, including any or a combination of the genes encoded on the virus, such as the ten gene segments of a reovirus. For example, mutation of a reovirus S1 or S4 gene, as compared to the reovirus wild-type gene, may be coupled with 1, 2, 3, 4, 5 or more mutations on the ten gene segments of the reovirus.

A variety of biological assays may be combined with any of the foregoing methods for generating an attenuated reovirus, for purposes of selecting for an attenuated reovirus having a desirable phenotype. By way of non-limiting example, an attenuated reovirus that is deficient in σ1 protein expression may be further selected on the basis of its decreased (e.g., in a statistically significant manner relative to wild-type reovirus) adhesion to target host cell surfaces, or of decreased infectivity in normal tissues or decreased damage to cells (in vivo or ex vivo) while retaining oncolytic effects toward malignant cells. Various methods may be used to generate attenuated reoviruses, including methods, e.g., described in U.S. Application 60/704,604.

Attenuated reoviruses are contemplated that may be genetically homogeneous or that may comprise a genetically heterogeneous reoviral population, such as may be the result of mutation and/or of assortative recombination within an infected host cell among reoviral genome segments derived from two or more distinct polymorphic reoviral strains with which the cell has been infected. Attenuated reoviruses described herein comprise a heritable mutant reovirus S1 gene, and as such the invention expressly does not include wt reovirus particles that comprise a wt S1 gene, even where such particles result from subjecting a wt reovirus to proteolytic conditions or otherwise artificially stripping a wt reovirus of σ1 capsid protein (e.g., Chandran et al., 1999; Chandran et al., 2001).

II. Cancer Therapies

The present invention provides, in certain embodiments, methods for cancer therapies. For example, individuals with hematopoietic or solid cancers that are treated by myeloablative therapy may subsequently receive hematopoietic stem cell rescue using purged bone marrow tissue that was harvested from the individual prior to chemotherapy; in these embodiments, the bone marrow may be treated with an attenuated reovirus in order to remove or kill neoplastic cells while reducing or eliminating damage to hematopoietic stem cells.

The use of patients' own adult stem cells for cell therapies can circumvent the problems of host immunity, graft-versus-host disease and ethical issues. Human adult stem cells have thus been widely evaluated for various tissue regeneration therapeutic modalities. However, it has been reported that spontaneous transformation can occur during the in vitro culture expansion of adult stem cells (Tolar et al., 2007; Romano, 2005). Therefore, a proper purging strategy to eliminate spontaneously transformed cells present in culture expanded adult stem cells for a safer use in transplantation and tissue regeneration. Although wild-type reovirus has shown utility in removing cancerous cells present in autologous hematopoietic stem cell populations in vitro (Thirukkumaran et al, 2003; Thirukkumaran et al., 2005), wild-type reovirus is known to cause various viral pathogenesis in immunodeficient hosts and in some cases is associated with viral myocarditis and CNS disease including humans (Dichter et al., 1984; Flamand et al., 1991; Richardson et al., 1994; Oberhaus et al., 1997; Weiner et al., 1977; Weiner et al., 1980; Mann et al., 2002; Terheggen et al., 2003; Loken et al., 2004; Kim et al., 2006).

Attenuated reoviruses can specifically target transformed cells for viral infection while exerting a reduced viral pathogenesis in immunocompromised hosts, and sparing stem cells and their developmental potential. An attenuated reovirus, such as the AV reovirus as described herein, may be used as a purging agent to eliminate transformed cells present in the culture expanded adult stem cells such as mesenchymal, epithelial and neural stem cells. The inventors anticipate that the present invention may be used with virtually any adult or embryonic stem cell line that is presently known or subsequently discovered.

The presence of a malignant condition in a subject refers to the presence of dysplastic, inappropriately proliferating, cancerous and/or transformed cells in the subject, including, for example neoplastic, tumor, non-contact inhibited or oncogenically transformed cells, or the like (e.g., melanoma, carcinomas such as adenocarcinoma, squamous cell carcinoma, small cell carcinoma, oat cell carcinoma, etc., sarcomas such as fibrosarcoma, chondrosarcoma, osteosarcoma, etc., hepatoma, neuroblastoma, melanoma, hematopoietic malignancies such as lymphoma, leukemia, myeloma, etc.); which are known to the art and for which criteria for diagnosis and classification are established. Without being bound by any theory, the oncolytic properties of reoviruses may derive from viral tropism for malignantly transformed cells in concert with a susceptible intracellular environment, for example, impaired PKR phosphorylation in Ras-activated cells as described above.

The presently described attenuated reoviruses are contemplated for use in a wide range of activated oncogene-associated malignant conditions, i.e., malignant conditions in which a mutation or other structural or functional alteration to an oncogene or an oncogene product renders the oncogene constitutively active with deleterious consequences (e.g., unregulated cell growth), including malignancies wherein the activated oncogene is Ras or an upstream or downstream component of the Ras pathway, and also including other oncogene-associated malignant conditions, for example, wherein the activated oncogene may be at least one of abl, akt, cbl, ets, mos, Bcl-2, crk, fos, fms, HER2, hTERT, jun, kit, myb, myc, raf, rel, sos, src, and yes. For a review of viral oncogenes see Bishop (1985); Vogelstein et al. (2004).

For instance, resistance to reoviral oncolysis has been observed by the present inventors in human cancer cells having an activated Ras gene and intact PKR phosphorylation, suggesting that reoviral oncolysis is not exclusively dependent on the Ras-status of cancer cells (Kim et al., 2006). Accordingly, certain embodiments relate to attenuated reoviruses that may be used in methods of treating an activated oncogene-associated malignant condition, which methods comprise administering an effective amount of an attenuated reovirus as described herein to a subject having such a malignant condition, under conditions and for a time sufficient for the attenuated reovirus to mediate an oncolytic effect.

Oncolytic activity of the attenuated reovirus described herein need not, however, be limited to activity directed against malignant conditions associated with a known oncogene. Without wishing to be bound by theory, attenuated reovirus oncolytic activity may proceed, for example, via host cell mechanisms of innate immunity (e.g., Martinon, 2005; Philpott et al., 2004) and/or via host cell mechanisms of intrinsic immunity (e.g., Bieniasz, 2004). Additionally according to non-limiting theory, a number of other genes and/or gene products that are not typically regarded as oncogenes or oncogene products per se have been implicated in tumorigenesis or in mechanisms underlying predisposition to cancer (Vogelstein et al., 2004; Futreal et al., 2004), such that certain invention embodiments disclosed herein contemplate attenuated reoviruses having oncolytic activity toward malignancies associated with mutations in oncogenes and/or in non-oncogenes, for instance, tumor-suppressor genes and stability genes. Determination of the suitability of the presently disclosed attenuated reoviruses for oncolytic application to a particular malignant condition may include may be achieved using in vitro or in vivo methodologies such as those described herein or known to the art, for example by obtaining a biological sample comprising tumor cells (e.g., Monks et al., 1991) and administering thereto the attenuated reovirus under conditions and for a time sufficient to detect an oncolytic effect.

A. Removal of Virus From Cellular Compositions

In certain embodiments, it may be desirable to remove an attenuated reovirus from a cellular composition, for example, after a period of time sufficient to allow for killing of a neoplastic cell (if present). For example, bone marrow may be taken from an individual and treated with an attenuated reovirus to destroy neoplastic cells; however, prior to re-implanting the bone marrow in the individual (e.g., an immunocompromised cancer patient) it may be desirable to destroy, eliminate and/or remove the virus from the composition. In these embodiments, an anti-viral agent may be added to the cellular composition. These agents include anti-reovirus antibodies and complements, inhibitors of essential viral enzymes such as RNA-directed RNA polymerase inhibitors, or agents that interfere with successful viral packaging, assembly or release from infected cells.

In certain embodiments, peptidyl fluoromethylketones (PFMKs) may be applied to the cellular composition to inhibit or eliminate reovirus from the composition. U.S. Provisional Application Ser. No. 60/906,706, incorporated herein by reference in its entirety, describes peptidyl fluoromethylketones (PFMKs) for inhibiting viral replication and is incorporated herein by reference in its entirety without disclaimer.

Additional purification steps, including washing and/or centrifuging the cells may be employed to further remove virus and/or dead cells from a cellular composition. These methods are known in the art and include methods that would enrich for desirable cell types, including fluorescence activated cell sorting or adhesion based methods that would enable positive selection of intended cells, such as stem cell populations.

B. Combination In Vitro Approaches

In order to increase the effectiveness of the selective killing of neoplastic cells by an attenuated reovirus (e.g., in a mixed cell population in vitro), it may be desirable, in certain embodiments, to contact the cells with an additional anti-cancer agent such as a chemotherapeutic agent or, in some instances, a gene therapy. The term "chemotherapy" refers to the use of drugs to treat cancer. A "chemotherapeutic agent" is used to connote a compound or composition that is administered in the treatment of cancer. One subtype of chemotherapy known as biochemotherapy involves the combination of a chemotherapy with a biological therapy.

Chemotherapeutic agents include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP 16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, corticosteroid hormones, mitotic inhibitors, and nitrosoureas, hormone agents, miscellaneous agents, and any analog or derivative variant thereof.

The attenuated reoviral purging of neoplastic cells may precede, be co-current with and/or follow the application of other agent(s) to a cell population by intervals ranging from minutes to weeks. For example, in such instances, it is contemplated that one may contact a mixed cell population, tissue or organ with one, two, three, four or more modalities substantially simultaneously (i.e., within less than about a minute) as the attenuated reovirus. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the attenuated reovirus.

Various combination regimens of the attenuated reovirus and one or more agents may be employed. Non-limiting examples of such combinations are shown below, wherein a composition atteunated reovirus is "A" and an anti-cancer agent is "B":

A/B/A  B/A/B  B/B/A  A/A/B  A/B/B  B/A/A  A/B/B/B  B/A/B/B

B/B/B/A  B/B/A/B  A/A/B/B  A/B/A/B  A/B/B/A  B/B/A/A

B/A/B/A  B/A/A/B  A/A/A/B  B/A/A/A  A/B/A/A  A/A/B/A

In embodiments where an attenuated reovirus is used to purge or kill neoplastic cells in a cellular compositions (e.g., bone marrow transplant), it is anticipated that one or more additional therapies will be administered to the patient. These therapies include therapies known in the art, such as chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

III. Safety of Attenuated Reovirus Exposure to Stem Cells

Most human cancers derive from a single cell targeted by genetic and epigenetic alterations that initiate malignant transformation. Progressively, these early cancer cells give rise to different generations of progeny that accumulate additional mutations, as tumor formation seems to be a multi-hit process. In normal tissue, adult stem cells generally maintain the steady state between cells that loose their functionality and regeneration thereof, as they can simultaneously perpetuate themselves and generate differentiated daughter cells. An understanding of a proto-oncogene and tumor suppressor networks has evolved within the last years that control cancer cell proliferation, but also stem cell self-renewal. Imbalances and transforming mutations within these networks may hence lead to improper cell-divisions that cause cancer (for review see Pardal et al., 2005; Martinez-Climent et al., 2006).

Despite a better understanding of the biology of tumor cells, decreasing mortality rates can be ascribed to early detection and prevention rather than treatment methods, which have not significantly changed over the past decade. Initially identified as a benign (orphan) virus isolated from human respiratory and gastrointestinal tracts, the reovirus has long been recognized for its striking cytocidal activity upon infection of certain types of transformed cells (Duncan et al., 1978; Hashiro et al., 1977). More recently, the molecular basis of this natural oncolytic capacity of reovirus has been established by linking viral oncolysis to cellular oncogenic Ras signaling pathways (Coffey et al., 1998; Strong et al., 1998, Norman et al., 2004). Subsequently, considerable efforts have been undertaken to develop cancer therapeutics using naturally occurring reoviruses (Norman et al., 2005). However, despite reoviral tropism for, and lysis of, Ras-activated tumor cells, efforts to use reoviruses as therapeutic oncolytic agents have been hampered by several factors, including (i) wt reoviral tropism is not strictly limited to cancer cells and naturally occurring reoviruses may not be clinically innocuous, with animal models revealing reoviral infection of cardiac myocytes (DeBiasi et al., 2004; Terheggen et al., 2003; Loken et al., 2004; Kim et al., 2006); (ii) and reoviruses induce many undesirable phenomena such as hemorrhage, fibrosis, hepatitis, pancreatitis, necrotizing encephalitis and myocarditis (Sabin, 1959; Weiner et al., 1977; Baty et al., 1993; Loken et al., 2004; Jun et al., 2003; Richardson et al., 1994; Mann et al., 2002); and (iii) as with other oncolytic regimes, oncolytic reoviral treatments may also compromise the integrity of the host stem cell compartment. wt reovirus is known, for instance, to adversely affect the development of rat and murine embryos by retarding development and inhibiting blastocytst formation (Priscott, 1983; Heggie et al., 1979). Indeed, studies presented herein clearly shows that wt reovirus adversely affects murine embryonic stem cells in vitro and the developmental potential of stem cells in vivo. As shown in the examples below, wt reovirus preferentially infects primitive muscle and neural tissues, resulting in suppression of teratoma growth and development. However, AV reovirus did not affect embryonic stem cells in vitro and the developmental potential of stem cells in vivo.

wt reovirus preferentially infects primitive neural and muscle tissues. It has previously shown that wt reovirus infects neural tissues of suckling mice (Sabin, 1959; Weiner et al., 1977; Flamand et al., 1991; Oberhaus et al., 1997) and cardiac muscle tissues of adult SCID mice (Loken et al., 2004; Kim et al., 2006). In contrast, AV reovirus does not infect primitive neural and muscle tissues of teratomas as well-differentiated mature neural and muscle tissues are readily detectable in the AV reovirus-infected teratomas. Although there is no clear mechanistic explanation for this higher reoviral tropism toward normal muscle and neural tissues, genetic reassortment studies suggest that the reovirus S1 gene segment play a significant role in the reoviral virulence (Weiner et al., 1980; Weiner et al., 1977; Kauffman et al., 1983; Dichter et al., 1984; Haller et al., 1995). As the inventors have previously shown that AV reovirus acquired S1 gene attenuation during a persistent reovirus infection (Kim et al., 2006), this S1 attenuation may significantly contribute to the non-detectable AV reoviral pathogenesis toward primitive neural and muscle tissues.

Because of the high proliferative potential of embryonic stem cells (ESCs), many viruses including oncolytic viruses may have a capacity to adversely affect ESCs and their developmental potential. In fact, vesicular stomatitis virus (VSV) readily induced significant cytopathic effects on murine ESCs. The self-renewing potential of ESCs is maintained by the activation of the LIF-gp130-STAT3 pathway. At the end of this cascade, the core pluripotency-associated transcriptional regulators Sox-2, Oct-4 and Nanog sustain stemness of ESCs. Recently, a previously uncharacterized small molecule was identified that allows the propagation of ESCs in an undifferentiated, pluripotent state even in the absence of feeder cells (Chen et al., 2006). Biochemical and cellular experiments have led to the conclusion that this molecule, denoted pluripotin, acts through the dual inhibition of Ras GTPase-activating protein and ERK1 suggesting an involvement for Ras in promoting self-renewal. Murine ESCs indeed express a Ras-like gene (Eras). However, ERas-null ESCs maintain pluripotency, but show significantly reduced growth and tumorigenicity, which are rescued by expression of oncogenic ERas cDNA (Takahashi et al., 2003). Without wishing to be bound by any theory, it is possible that WT reovirus targets ESCs via its oncogenic Ras pathway.

Figure 5:
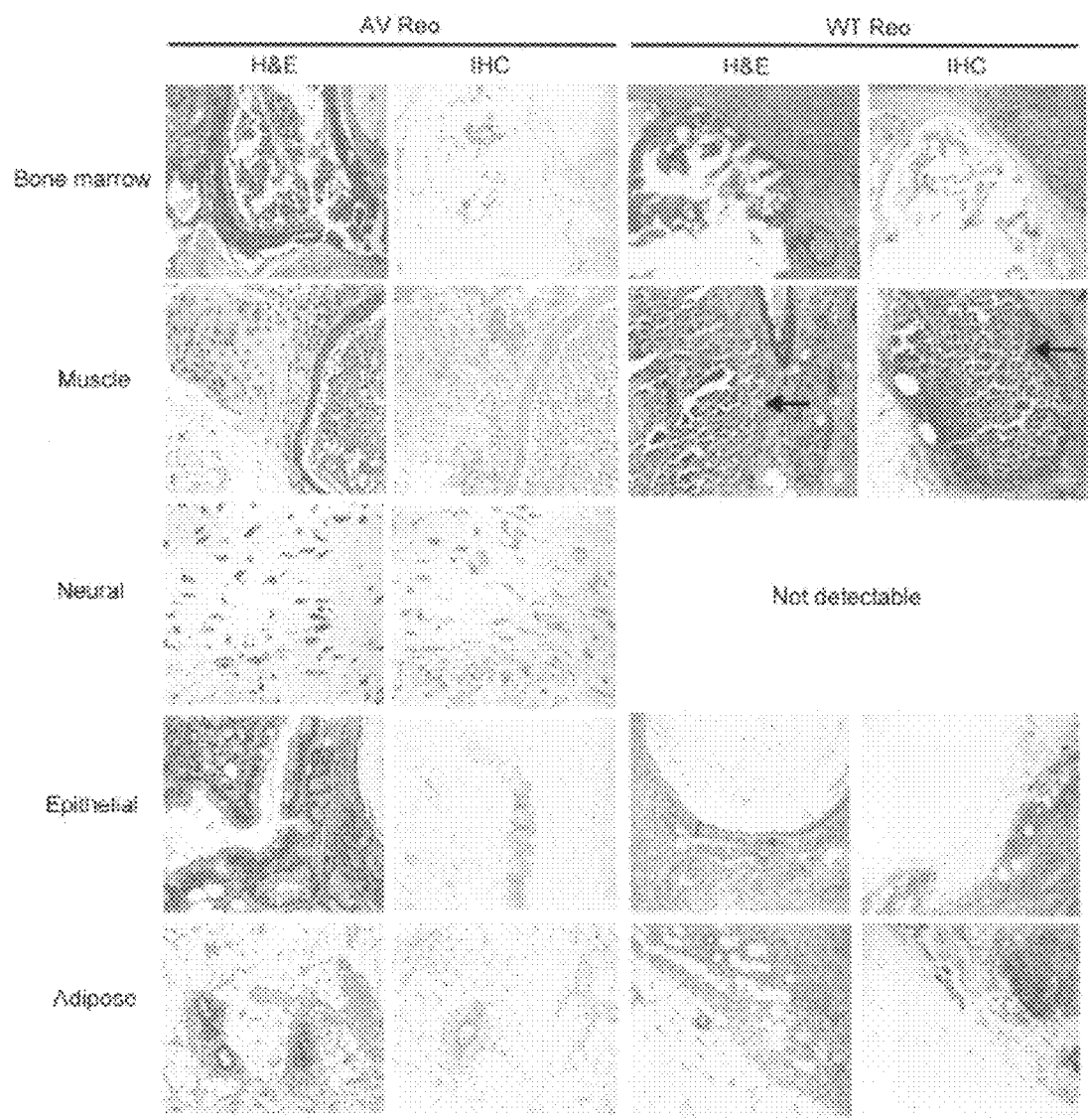
FIG. 5: Histological analysis of teratomas infected with wt or AV reovirus. R1 and MES1 Teratomas infected by wt or AV reovirus were taken from the mice at 23-58 days post-infection. Paraffin sections of the teratomas were examined by H&E (hematoxylin and eosion) and immunohistochemical (IHC) staining using reovirus antiserum. Brown staining represents reovirus protein positive and sections were counterstained with methyl green. Necrotic and reovirus antigen positive areas were co-localized in wt reovirus-infected teratomas. Primitive neural tissues were not detected in wt reovirus-infected teratomas. Primitive muscle tissues were undergoing necrotic damage in the presence of reoviral antigens (arrows). AV reovirus-infected teratomas did not show this pathology. Magnification: 10× or 20×.

AV reovirus clearly demonstrated sparing ESCs and their developmental potential. Moreover, the inventors speculate that not only ESCs but also highly proliferative adult stem cells such as epithelial or hematopoietic stem cells could be affected by many viruses. In order to preserve tissue regeneration capacity, evaluation of viral pathogenesis against embryonic or/and adult stem cell will be required to mediate an optimal oncolytic viral therapy. By exploiting the non-pathogenic nature toward stem cells, oncolytic AV reovirus may be useful for stem cell purging strategies during anti-cancer therapy. For instance, hematopoietic stem cell rescue after high dose cytotoxic therapy has been widely used for treatment of many hematopoietic and solid cancers in clinics. Although wt reovirus has shown a potential for removing cancerous cells present in autologous hematopoietic stem cell populations (Thirukkumaran et al., 2003), AV reovirus could be a safer alternative to spare not only normal hematopoietic stem cells but also other adult stem cells and ESCs, and avoid unwanted wt reovirus-mediated complications. The non-pathogenic nature of AV and wt reovirus toward hematopoietic stem cells is further supported by the reovirus infected teratoma model since bone marrow development is not affected by either AV or wt reovirus treatment, as shown in FIG. 5. Moreover, since opportunistic viral infections are important causes of morbidity and mortality in patients undergoing hematopoietic stem cell transplantation (Bruno et al., 2003; Crippa et al., 2002; Hebart et al., 2004; De Rosa et al., 2004), a safer oncolytic virus should provide a greater benefit for the purging strategy. Another potential utility of AV reovirus oncolysis may lie in pediatric cancers. Since conventional chemo/radiation therapies may cause more significant damage to the growing normal tissues in a child than in adults, the stem cell sparing AV reovirus may offer less damaging effects in children during anti-cancer therapy. Taken together, AV reovirus holds a great potential for various anti-cancer therapeutic strategies since AV reovirus spares not only normal tissues of immunodeficient hosts compared to wt reovirus (Kim et al., 2007) but also ESCs and their developmental potential while retaining anti-tumor effects. With greatly enhanced specificity, AV reovirus may be useful in targeting various types of cancers in a clinical setting.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Cell Lines.

Murine R1 and D3 embryonic stem cell lines were purchased from the American Type Culture Collection (ATCC). The cells were maintained in high glucose DMEM, 15% FCS (selected batches), 50 U/ml Penicillin and 50 μg/ml Streptomycin, 1% non essential amino acids and 0.1 mM b-Mercaptoethanol as described (zur Nieden et al., 2001). Thousand U/ml Leukemia Inhibitory Factor (LIF) were added to the culture medium to sustain pluripotency. The cultures were passaged when 80% confluent, usually every second day. All medium components were purchased from Invitrogen. Murine MES1 embryonic stem cells were isolated from 3.5 day post coitum embryos of the 129 IM/SvJ substrain at the blastocyst stage. MES1 were routinely grown as described for R1 and D3 ESCs. Spontaneous differentiation was induced by removal of LIF and formation of embryoid bodies in hanging drops as it was done previously (zur Nieden et al., 2003).

wt and AV Reovirus Preparation.

The wt reovirus serotype 3 Dearing strain used in these studies was propagated in L929 cells and purified as described previously (Smith et al., 1969). AV reovirus derived from the HTR1 culture (Kim et al., 2006) was purified by the same method used in the wt reovirus preparation except AV reovirus was propagated in HT1080 cells. Reovirus was added at a multiplicity of infection (MOI) of 5-10 and maintained at 37° C. for 48-72 hrs. After viral cytopathic effects were observed (typically 20-30% cell lysis), the virus was purified from pelleted cells, as described previously (Smith et al., 1969). CsCl centrifugation of the virus was done using an SW41 rotor at 35,000 rpm for 7-8 hrs. The banded virus was collected and dialyzed extensively against 150 mM NaCl, 10 mM $MgCl_2$, and 10 mM Tris (pH 7.5).

Immunoblot and Fluorescence-Activated Cell Sorting (FACS) Analysis.

Cell lysates were prepared by sonication in a buffer containing 10 mM Tris (pH 7.4), 2 mM EDTA, 1% NP-40, 50 mM mercaptoethanol, 100 μg/ml leupeptin and 2 μg/ml aprotinin at the time points indicated. The lysates were then cleared by centrifugation at 16,000 g for 15 min, normalized for protein amount, mixed with SDS sample buffer, boiled for 5 min and stored at −70° C. After separation by SDS-PAGE, proteins were transferred to nitrocellulose membranes and detected by immunoblot hybridization. The primary antibodies (Abs) were as follows: anti-reovirus polyclonal Ab (Kim et al., 2006), and anti-actin Ab (Cell Signaling, Beverly, Mass.). The secondary antibody was horseradish peroxidase-conjugated anti-mouse Ab or horseradish peroxidase-conjugated anti-rabbit Ab (Pierce Biotech, Rockford, Ill.). For FACS analysis, cells were trypsinized and fixed using cytofix/cytoperm solution (PharMingen, San Diego, Calif.). The fixed and permeabilized cells were incubated with primary reovirus antiserum and secondary FITC conjugated anti-rabbit IgG (Cedarlane, Ontario, Canada), then analyzed by flow cytometry.

Animal Studies.

SCID mice (Charles River, Wilmington, Mass.) received a single subcutaneous implantation of $5 \times 10^6$ cells of murine ESCs (R1 or MES1). Twelve days after implantation, palpable teratomas were formed. The R1 teratomas were then injected with reoviruses [wt reo (wild-type reovirus), $1 \times 10^7$ PFU/tumor; n=5, AV reo (AV reovirus), $1 \times 10^7$ PFU/tumor: n=5, D reo (Dead, UV-inactivated reovirus): n=5] and teratoma growth was followed 21-70 days post-infection. For the MES1 teratoma experiment, 12-15 days after implantation, teratomas were intratumorally injected with reoviruses or PBS [wt Reo (wild-type reovirus), $10^7$ PFU per mouse); n=3, AV Reo (AV reovirus, $10^7$ PFU per mouse): n=3, PBS: n=3] and teratoma growth was followed 31-46 days post-infection. Mice were treated according to protocols approved by the University of Calgary Animal Care Committee. Teratoma growth was measured externally using calipers and the volume was determined by the equation $V=(L \times W2) \times 0.5$, where L is the largest dimension and W is the largest dimension perpendicular to L. Teratomas were taken from the mice at 21-70 days post-infection. The teratomas were then excised and fixed in 10% buffered formalin solution at room temperature, and the specimens were sent to the University of Calgary Histopathology Laboratory Research Service for routine histological analysis (H&E staining).

Histology and Immunohistochemistry.

For reovirus antigen detection (reovirus structural proteins), deparaffinized tumor sections were retrieved in a solution containing 50 mM Tris (pH 7.5), 120 mM NaCl, 0.2% Tween 20, and 0.1% Triton X-100. After blocking the sections with a solution containing 50 mM Tris (pH 7.5), 120 mM NaCl, 0.2% Tween 20, 0.1% Triton X-100 and 2% normal goat serum for 1 hr, the sections were immunostained with a solution containing 0.1% reovirus antiserum, 50 mM Tris (pH 7.5), 120 mM NaCl, 0.2% Tween 20, 0.1% Triton X-100 and 2% normal goat serum for 2 hr. As a secondary antibody, biotinylated goat anti-mouse antibody (Vector Laboratories, Burlingame, Calif.) was used at 1:100 in a solution containing 50 mM Tris (pH 7.5), 120 mM NaCl, 0.2% Tween 20, 0.1% Triton X-100 and 2% normal goat serum for 2 hr at room temperature. Detection was monitored by a diaminobenzidine tetrahydrochloride-based immunohistochemistry protocol according to the suggestions of the manufacturer (Vector Laboratories, Burlingame, Calif.). Dehydration was carried out in a series of graded ethanol solutions, followed by clarification in xylene. Slides were mounted with Vectamount (Vector Laboratories, Burlingame, Calif.) and stored at 25° C.

Electron Microscopy.

EM preparation of cells for electron microsocopy (EM) was performed by the University of Calgary Microscopy & Imaging Facility. Cells grown on glass slides were rinsed briefly with PBS (phosphate buffered saline) and fixed with 4% EM grade glutaraldehyde in 0.1M cacodylate buffer (pH 7.4) for 1 h at room temperature (RT). After washing three times with the same buffer, cells were post-fixed in 1% osmium tetroxide buffered with 0.1M cacodylate for 1 h at RT. Then cells were rinsed twice briefly with distilled water and stained en bloc for 30 min in 0.5% aqueous uranyl acetate. The cells were then dehydrated in an ethanol series and embedded in Spurr's low viscosity resin. Thin sections were cut with a diamond knife on a Reichert Ultracut E, stained with uranyl acetate and lead citrate and examined with a Hitach H-7000 transmission electron microscope at 75 kV.

Example 2—Results

Undifferentiated Embryonic Stem Cells are Highly Susceptible to WT Reovirus.

Although WT reovirus is known to adversely affect the development of rat and murine embryos by retarding development and inhibiting blastocytst formation (Priscott, 1983; Heggie et al., 1979), the potential reoviral cytopathogenicity on embryonic stem cells (ESCs) has not been fully examined. Thus, the inventors wished to examine reoviral cytopathogenicity on ESCs by detection of typical viral cytopathic effects upon reoviral infection in vitro. Murine ESCs were infected with wt reovirus at MOI of 20 to examine viral cytopathic effects and viral protein synthesis. As shown in FIG. 1, the ESCs showed extensive viral cytopathic effects (cell detaching and rounding) upon wild-type reoviral infection and a robust production of reoviral protein was detected in a time dependent manner with the first detectable viral proteins 12 hr post-infection. Therefore, ESCs are highly susceptible to wt reoviral infection.

AV Reovirus Exerts Significantly Reduced Viral Cytopathogenicity on Embryonic Stem Cells In Vitro.

Figure 2:
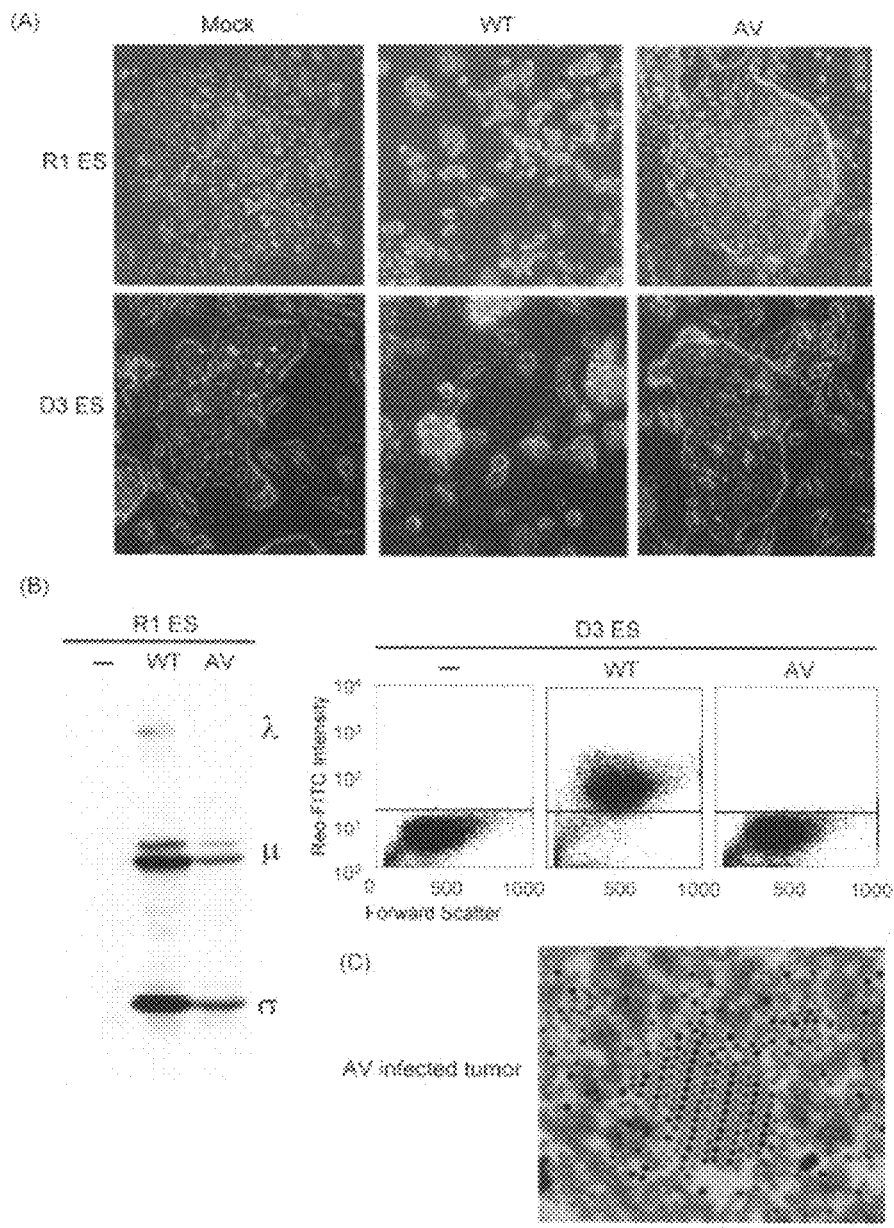
FIGS. 2A-B: Comparison of wt and AV reovirus (an S1 attenuated reovirus) cytopathogenicity on embryonic stem cells. Pluripotent murine ESCs (R1 and D3) were infected with wt or AV reovirus at MOI of 20.
FIG. 2C, Analysis of a AV reovirus infected HCT 116 xenografted tumor (Kim et al., 2006) by electron miscroscopy. Robust AV reovirus replication is detected in the tumor sites.

The inventors have previously shown that AV reovirus exerts a significantly reduced viral pathogenesis without compromising oncolytic activity in vivo (FIG. 2C). To further evaluate AV reoviral cytopathogenicity, the inventors wished to compare wt and AV reoviral cytopathogenicity on ESCs. Thus the inventors challenged murine ESCs with wt and AV reovirus. As shown in FIG. 2, AV reovirus did not cause significant viral cytopathogenicity. Upon infection of two murine embryonic stem cell (ESC) lines, R1 and D3 ESCs, AV reovirus did not cause detectable viral cytopathic effects (FIG. 2A) and reoviral protein synthesis and antigen detection were significantly reduced compared to wt reovirus infection (FIG. 2B). Taken together, although ESCs are highly susceptible to wt reovirus infection, AV reovirus minimally infects ESCs and does not induce typical viral cytopathic effects in vitro. Therefore, AV reovirus displays much greater specificity by sparing normal ESCs.

AV Reovirus does not Affect the Developmental Potential of ESCs in Teratoma Model.

Figure 3:
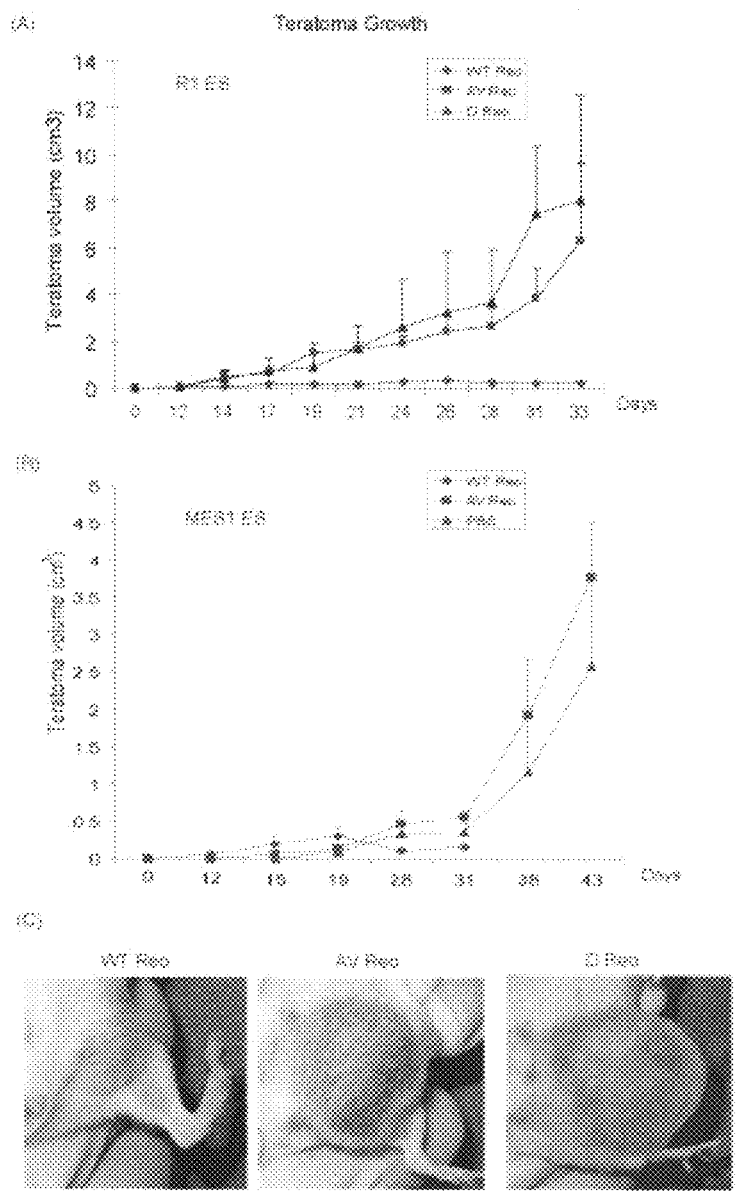
FIGS. 3A-C: Comparison of teratoma growth upon wt or AV reovirus infection.

Because wt reovirus is known to adversely affect the development of rat and murine embryos by retarding development and inhibiting blastocytst formation (Priscott, 1983; Heggie et al., 1979) and AV reovirus exerts a significantly reduced viral cytopathogenicity on ESCs in vitro, the inventors wished to further compare wt and AV reoviral pathogenesis in vivo. For an in vivo viral pathogenesis study, the inventors adopted a murine teratoma model since pluripotent ESCs have a capacity to develop mature teratomas with a high level of differentiation upon xenograft implantation in vivo (Sasaki et al., 2005). Thus, the inventors used SCID mice xenografted with murine ESCs to develop teratomas. Once palpable teratomas were formed following implantation of ESCs (12 days post-implantation), wt and AV reoviruses were administered intratumorally and teratoma growth was monitored (FIGS. 3A-C). Consistent with the in vitro observations, growth of teratomas infected with wt reovirus was significantly suppressed compared to AV reovirus- or mock-infected teratomas (FIGS. 3A-C).

Figure 4:
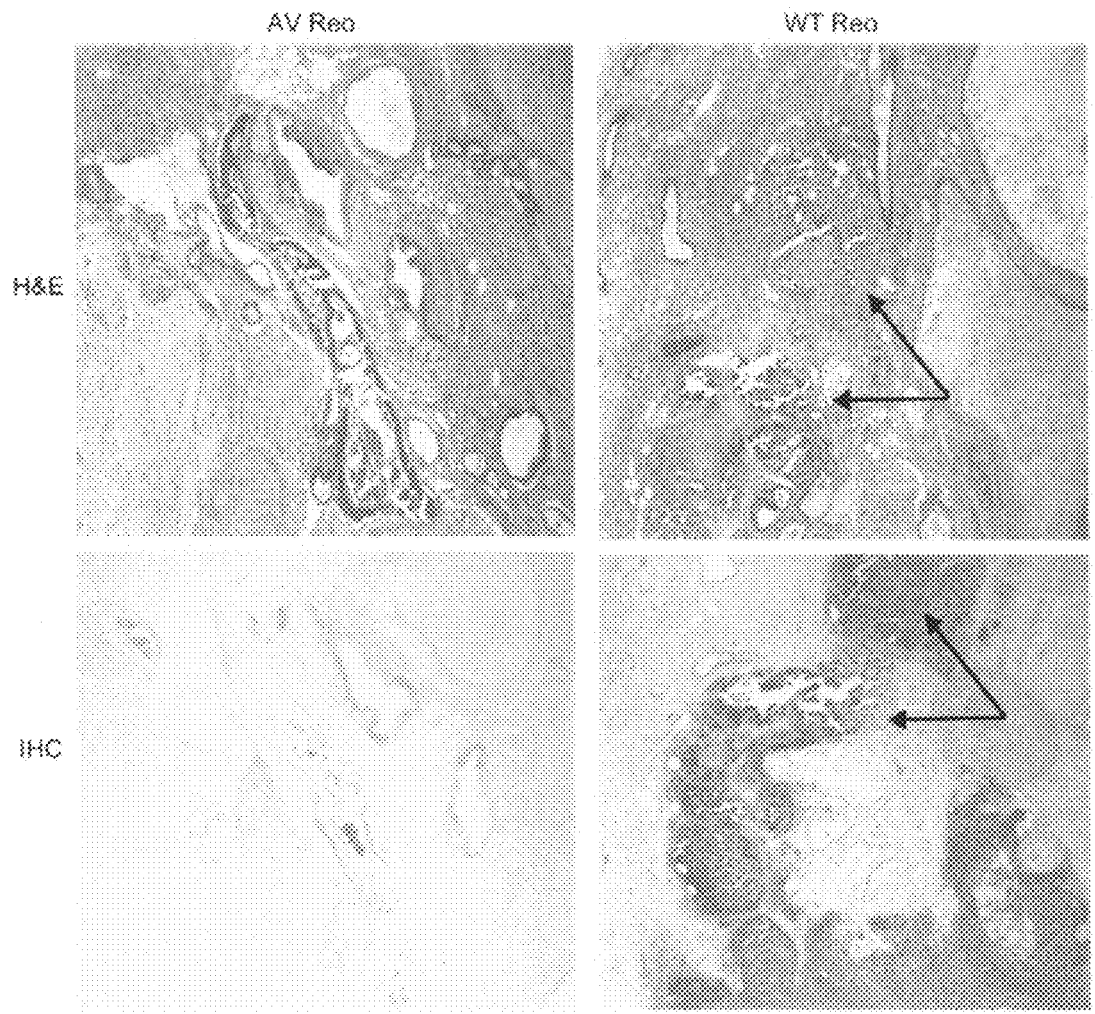
FIG. 4: Immunohistochemical analysis of teratomas infected with wt or AV reovirus. R1 Teratomas infected by wt or AV reovirus were taken from the mice at 23 days post-infection. Paraffin sections of the teratomas were examined by H&E (hematoxylin and eosion) and immunohistochemical (IHC) staining using reovirus antiserum. Brown staining represents reovirus protein positive and sections were counterstained with methyl green. Widespread necrotic and reovirus antigen positive areas were co-localized in wt reovirus infected teratomas (arrows indicate necrotic and reoviral protein positive area), but not in AV reovirus infected teratomas. Magnification: 4×

Histological analysis of the wt or AV infected teratomas revealed that AV reovirus-treated teratomas showed a high level of differentiation with various mature tissues, whereas wt reovirus treated teratomas showed extensive necrotic damage near the various mature tissues (FIG. 4 upper panels). Immunohistochemical analysis further revealed that the necrotic places were co-localized with reovirus antigen positive areas in the wt reovirus infected teratomas, whereas AV reovirus infected teratomas did not show reoviral antigens (FIG. 4 lower panels). Therefore, consistent with the in vitro observations, wt reovirus highly infects teratomas and AV reovirus does not infect mature tissues in teratomas.

Figure 6:
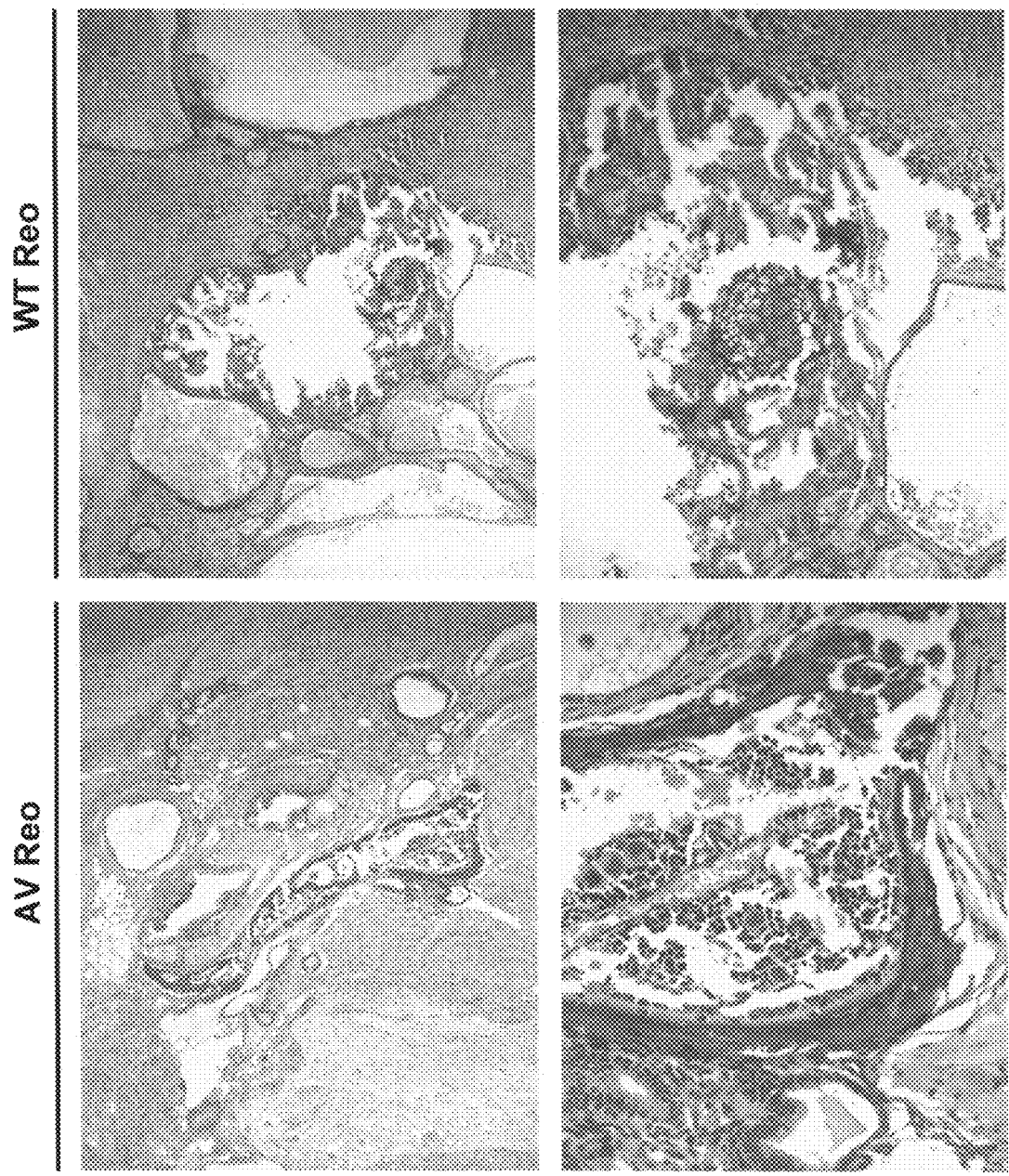
FIG. 6: AV reovirus does not affect bone marrow development in vivo. R1 teratomas infected by WT or AV reovirus were taken from the mice at 23 days post-infection. Paraffin sections of the teratomas were examined by H&E (hematoxylin and eosion). While bone marrow formation of teratoma treated with WT reovirus shows disorganized structure and necrotic mononuclear cell population, bone marrow formation of teratoma treated with AV reovirus shows structurally and morphologically intact mononuclear cell population. Magnification: 5× (upper panel), 10× or 20× (lower panel).
Figure 7:
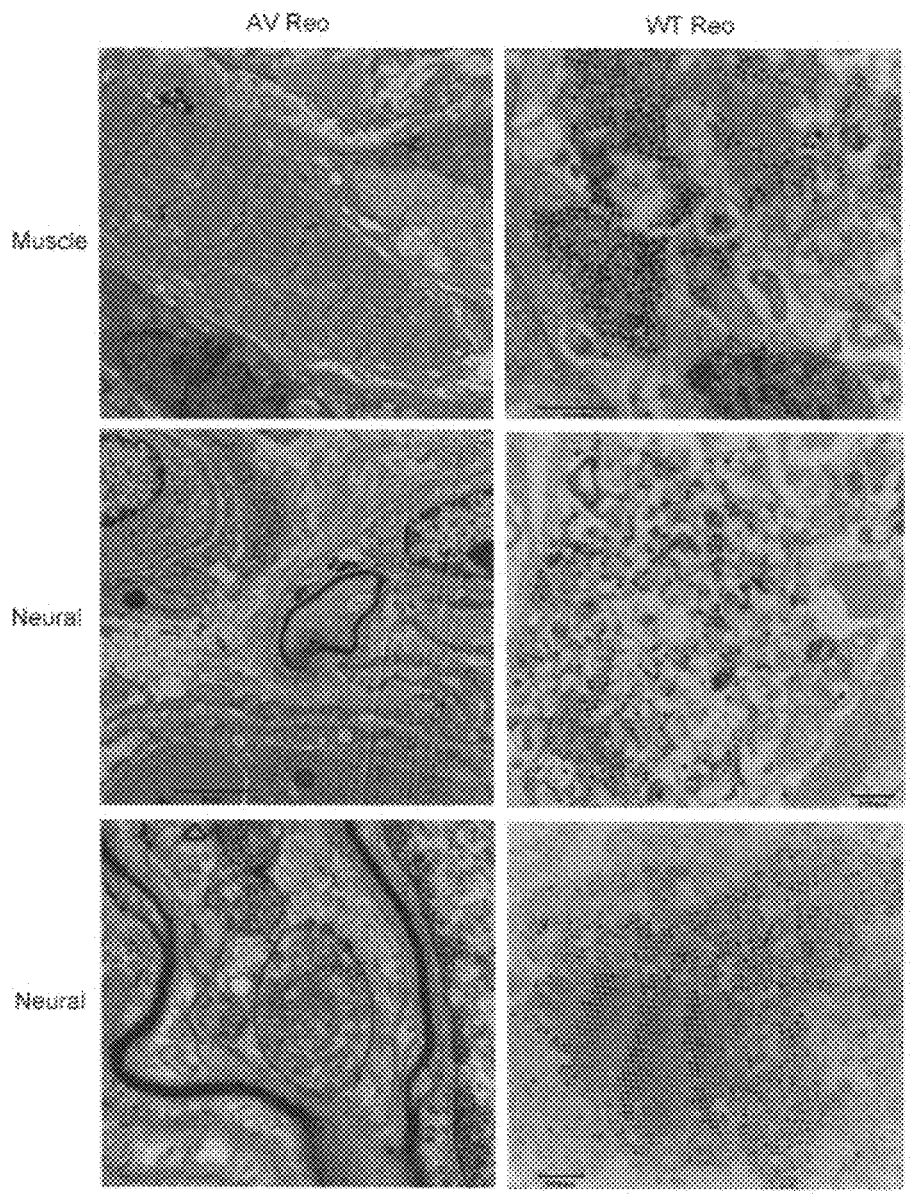
FIG. 7: An analysis of teratomas infected with wt or AV reovirus using electron microscopy. R1 and MES1 Teratomas infected by wt or AV reovirus were taken from the mice at 23-58 days post-infection. EM fixed teratomas were examined under an electron microscope. AV reovirus-infected teratomas show well-differentiated muscle and neural tissues (myelin structure) (upper: primitive muscle tissue, 4,000×, Middle: primitive neural tissue, 5,000×; bottom: primitive neural tissue, 15,000×). wt reovirus-infected teratomas show extensive tissue damage accompanied with high reovirus replication activity (viral inclusions).

Because teratomas were widely infected by wt reovirus, the inventors further examined susceptible primitive tissues affected by wt reovirus. As shown in FIG. 5, primitive muscle and neural tissues were highly susceptible to wt reovirus infection, whereas these tissues were intact in the AV reovirus infected teratomas. Epithelial like tissue, and chondroid/adipose tissues were relatively resistant to wt reovirus infection (FIG. 5). Importantly, in comparison with AV and WT reovirus effects on bone marrow formation, AV reovirus does not affect bone marrow formation and hematopoiesis derived from embryonic stem cell while WT reovirus significantly affects bone marrow formation and hematopoiesis (less mononuclear cell population and necrotic hematopoiesis) in vivo as shown by H&E staining analysis (FIG. 6). Therefore AV reovirus holds a great potential of virally purged autologous bone marrow transplantation for the treatment of hematological malignancies. Consistent with this, analysis of teratomas by electron microscopy also showed extensive viral replication in the wt reovirus-infected teratomas, whereas mature muscle and neural tissues were intact in the AV reovirus infected teratomas without evidence of viral replication (FIG. 7). Taken together, WT reovirus preferentially infects primitive neural and muscle tissues of teratomas, whereas AV reovirus does not infect these tissues.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,994,858
U.S. Patent Publn. 2001/0048919
U.S. Patent Publn. 2002/0006398
U.S. Patent Publn. 2002/0037543
U.S. Patent Publn. 2004/0109878
U.S. Patent Publn. 2005/0026289
U.S. Patent Publn. 2006/0029598
U.S. Appn. Ser. 60/704,604
U.S. Appn. Ser. 60/906,706
Ahmed et al., *Cell* 28:605, 1982.
Altschul et al., *Nucl. Ac. Res.*, 25:3389, 1997.
Altschul, *J. Mol. Biol.* 219:555-565, 1991.
Ausubel et al., *Current Protocols in Molecular Biology*, Greene Publ. Assoc. Inc. & John Wiley & Sons, Inc., MA, 1993.
Ausubel et al., *Current Protocols in Molecular Biology*, John Wiley & Sons, NY, 1989.
Baty and Sherry, *J. Virol.*, 67:6295-6298, 1993.
Bieniasz, *Nature Immunol.*, 5:1109, 2004.
Bishop, *Cell*, 42(1):23-38, 1985.
Bruno et al., *Biol. Blood Marrow Transplant.*, 9:341-352, 2003.
Chandran et al., *J. Virol.*, 73:3941, 1999.
Chandran et al., *J. Virol.*, 75:5335, 2001.
Chappell et al., *J. Virol.*, 71:1834, 1997.
Chappell et al., *J. Virol.*, 74:8472, 2000.
Chen et al., *Proc. Natl. Acad. Sci. USA*, 103:17266-17271, 2006.
Coffey et al., *Science*, 282:1332-1334, 1998.
Connolly et al., *J. Virol.*, 75:4029, 2001.
Crippa et al., *Biol. Blood Marrow Transplant.*, 8:281-289, 2002.
De Rosa et al., *Int. J. Hematol.*, 79:85-91, 2004.
DeBiasi et al., *J. Virol.*, 78:11040-11050, 2004.
Dichter and Weiner, *Ann. Neurol.*, 16:603-610, 1984.
Duncan et al., *Virology*, 182:810, 1991.
Duncan et al., *J. Virol.*, 28:444-449, 1978.
Duursma and Agami, *Semin. Cancer Biol.*, 13:267-273, 2003.
Ernst et al., *Proc. Nat. Acad. Sci. USA*, 82:48, 1985.
Fernandes et al., *J. Biol. Chem.*, 269:17043, 1994.
Flamand et al., *J. Virol.*, 65:123-131, 1991.
Futreal et al., *Nat. Rev. Cancer,* 4:177, 2004.
Giantini et al., *J. Virol.*, 52:984, 1984.
Glover, *DNA Cloning Vol. I and II*, IRL Press, Oxford, UK, 1985.
Greene and Wuts, In: *Protective Groups in Organic Synthesis*, $2^{nd}$ Ed.; Wiley, NY, 1999.
Haller et al., *J. Virol.*, 69(1):357-64, 1995.
Hames and Higgins, *Nucleic Acid Hybridization*, IRL Press, Oxford, UK, 1985.
Hashiro et al., *Arch. Virol.*, 54:307-315, 1977.
Hebartand Einsele, *Hum. Immunol.*, 65:432-436, 2004.
Heggie and Gaddis, *Pediatr. Res.*, 13:937-941, 1979.
Henikoff et al., *Proc. Natl. Acad. Sci. USA,* 89:10915-10919, 1992.
Hirasawa et al. *Cancer Res.*, 15:348-353, 2003.
Hoyt et al., *J. Virol.*, 79:2743, 2005.
Jacobs et al., *Virology*, 147:9-18, 1985.
Jun and Yoon, *Diabetes Metab. Res. Rev.*, 19:8-31, 2003.
Kauffman et al., *Virology,* 124:403-410, 1983.
Kaye et al., *J. Virol.*, 59(1):90-7, 1986.
Kim et al., *Proc. Natl. Acad. Sci. USA,* 2007 (submitted).
Kim *Oncogene*, 26(28):4124-34, 2007.
Larson et al., *Virology*, 201:303, 1994.
Lee et al., *Virology*, 108:156, 1981.
Lee et al., *BioEssays*, 16:199, 1994.
Leone et al., *J. Biol. Chem.*, 271:8466, 1991.
Loken et al., *Cancer Biol. Ther.*, 3:734-738, 2004.
Mah et al., *Virology*, 179:95, 1990.
Maniatis et al., Molecular Cloning, Cold Spring Harbor Laboratory, Plainview, N.Y., 1982.
Mann et al. *Virology*, 303:213-221, 2002.
Martinez-Climent et al., *Clin. Transl. Oncol.*, 8:647-663, 2006.
Martinon, *Trends Immunol.*, 26:447, 2005.
Monks et al., *J. Nat. Canc. Inst.*, 83(11):757-66, 1991.
Nagata et al., *Virology*, 160:162, 1987.
Norman et al. *Proc. Natl. Acad. Sci. USA,* 101:11099-11104, 2004.
Norman et al. *Drug Discov. Today*, 10:847-855, 2005.
Oberhaus et al. *J. Virol.*, 71:2100-2106, 1997.
Pardal, et al. *Cold Spring Harb. Symp. Quant. Biol.*, 70:177-185, 2005.
PCT Appln. PCT/US2006/029881
Philpott et al., *Mol. Immunol.*, 41:1099, 2004.
Priscott, *Br. J. Exp. Pathol.*, 64:467-473, 1983.
Richardson et al. *J. Gastroenterol. Hepatol.*, 9:264-268, 1994.
Romano, *Drug News Perspect.*, 18(2): 128-34, 2005.
Sabin, *Science*, 130:1387-1389, 1959.
Sambrook et al., *Molecular Cloning*, Second Ed., Cold Spring Harbor Laboratory, Plainview, N.Y., 1989.
Sarkar et al., *J. Virol.*, 54:720, 1985.
Sasaki et al. *Stem Cells*, 23:1304-1313, 2005.
Smith et al. *Virology*, 39:791-810, 1969.
Strong et al. *EMBO J*, 17:3351-3362, 1998.
Takahashi et al. *Nature*, 423:541-555, 2003.

Terheggen et al. *Eur. J. Clin. Microbiol. Infect. Dis.,* 22:197-198, 2003.
Thirukkumaran et al. *Blood,* 102:377-387, 2003.
Thirukkumaran et al., *Bone Marrow Transplant.,* 35(11):1055-64, 2005.
Tolar et al., *Stem Cells,* 25(2):371-9. 2007.
Turner et al., *Virology,* 186:219, 1992.
Tyler and Fields, In: *Fields' Virology*, Fields, Knipe, Howley, (Eds.), Lippincott-Raven, Philadelphia, 1597-1623, 1996.
Tyler, In: *Fields Virology*, Knipe and Howley (Eds.), Lippincott Williams & Wilkens, Philadelphia, 1729-1745, 2001.
Vogelstein et al., *Nature Medicine,* 10:789, 2004.
Weiner et al., *J. Infect. Dis.,* 141(5):609-16, 1980.
Weiner et al. *Proc. Natl. Acad. Sci. USA,* 74:5744-5748, 1977.
Wilson et al., *J. Virol.,* 68(10):6458-65, 1994.
zur Nieden et al. *Differentiation,* 71:18-27, 2003.
zur Nieden et al. *Toxicol. In vitro.,* 15:455-461, 2001.

What is claimed is:

1. A method of killing or removing a neoplastic cell from a cellular composition suspected of containing such neoplastic cells comprising contacting the cellular composition with an attenuated reovirus under conditions which result in oncolysis or killing of the neoplastic cell, wherein the attenuated reovirus is a human reovirus and wherein the attenuated reovirus is S1 attenuated reovirus possessing a S1 gene which produces a truncated S1 gene product.

2. A method of killing or removing a neoplastic cell from a cellular composition suspected of containing such neoplastic cells comprising contacting the cellular composition with an attenuated reovirus under conditions which result in oncolysis or killing of the neoplastic cell, wherein the cellular composition comprises stem cells and wherein the attenuated reovirus is S1 attenuated reovirus possessing a S1 gene which produces a truncated S1 gene product.

3. The method of claim 2, wherein the stem cells are embryonic stem cells.

4. The method of claim 3, wherein the embryonic stem cells are derived from cord blood or placenta.

5. The method of claim 2, wherein the stem cells are adult stem cells.

6. The method of claim 2, wherein the stem cells are hematopoietic stem cells.

7. The method of claim 6, wherein the hematopoietic stem cells are human hematopoietic stem cells.

8. The method of claim 6, wherein the cellular composition has been harvested from bone marrow.

9. The method of claim 6, wherein the cellular composition has been harvested from blood.

10. A method of killing or removing a neoplastic cell from a cellular composition suspected of containing such neoplastic cells comprising contacting the cellular composition with an attenuated reovirus under conditions which result in oncolysis or killing of the neoplastic cell, wherein the method further comprises contacting the attenuated reovirus-treated cellular composition with an anti-reovirus antibody, N-benzyloxycarbonyl-Phe-Ala-fluoromethylketone (Z-FA-FMK), an RNA-directed RNA polymerase inhibitor, or an antiviral agent, and wherein the attenuated reovirus is S1 attenuated reovirus possessing a S1 gene which produces a truncated S1 gene product.

11. The method of claim 10, wherein the method further comprises removing one or more attenuated reovirus from the cellular composition via washing, centrifugation, or fluorescence activated cell sorting.

12. A method of killing or removing a neoplastic cell from a cellular composition suspected of containing such neoplastic cells comprising contacting the cellular composition with an attenuated reovirus under conditions which result in oncolysis or killing of the neoplastic cell, further comprising transplanting or implanting the attenuated reovirus-treated cellular composition into a recipient, wherein the attenuated reovirus is S1 attenuated reovirus possessing a S1 gene which produces a truncated S1 gene product.

13. The method of claim 12, wherein the cellular composition comprises bone marrow or peripheral blood.

14. The method of claim 12, wherein the recipient is a human.

15. The method of claim 12, further comprising administering to the recipient a cancer therapy, a chemotherapy, or a radiation therapy.

16. The method of claim 12, wherein the recipient is immunocompromised.

17. The method of claim 16, wherein the recipient is immunocompromised due to a cancer therapy, a chemotherapy, or a radiation therapy.

18. The method of claim 16, wherein the recipient is immunocompromised due to HIV.

19. The method of claim 12, wherein said transplantation is autologous.

20. The method of claim 12, wherein said cellular composition comprises hematopoietic stem cells.

21. The method of claim 12 wherein the method reduces the risk of recurrence of cancer or tumors in the recipient and wherein the cellular composition comprises hematopoietic stem cells obtained from the recipient.

* * * * *